United States Patent
Mantell et al.

(10) Patent No.: US 10,493,220 B2
(45) Date of Patent: Dec. 3, 2019

(54) GAS RECIRCULATION SYSTEM AND METHOD

(71) Applicant: Northgate Technologies Inc., Elgin, IL (US)

(72) Inventors: Robert R. Mantell, Arlington Heights, IL (US); Donald Millar, Libertyville, IL (US); Patrick B. Millar, Libertyville, IL (US); Eric P. Andersen, Palatine, IL (US)

(73) Assignee: Northgate Technologies Inc., Elgin, IL (US)

( * ) Notice: Subject to any disclaimer, the term of this patent is extended or adjusted under 35 U.S.C. 154(b) by 0 days.

(21) Appl. No.: 15/200,534

(22) Filed: Jul. 1, 2016

(65) Prior Publication Data

US 2017/0000959 A1 Jan. 5, 2017

Related U.S. Application Data

(60) Provisional application No. 62/188,319, filed on Jul. 2, 2015.

(51) Int. Cl.
  *A61M 37/00* (2006.01)
  *A61M 13/00* (2006.01)
  *A61B 17/34* (2006.01)

(52) U.S. Cl.
  CPC ....... *A61M 13/006* (2014.02); *A61B 17/3474* (2013.01); *A61M 13/003* (2013.01);
  (Continued)

(58) Field of Classification Search
  CPC .......... A61B 17/3474; A61M 2205/15; A61M 2205/3337; A61M 2205/50;
  (Continued)

(56) References Cited

U.S. PATENT DOCUMENTS 4,561,431 A   12/1985   Atkinson
5,476,368 A   12/1995   Rabenau et al.
(Continued)

FOREIGN PATENT DOCUMENTS

WO   WO 94/01154   1/1994
WO   WO 98/06446   2/1998
(Continued)

OTHER PUBLICATIONS

Kay Ball, "Controlling Surgical Smoke: A Team Approach", IC Medical Inc., Phoenix, AZ, 2004, 27 pgs.
(Continued)

*Primary Examiner* — Rebecca E Eisenberg
(74) *Attorney, Agent, or Firm* — Brinks Gilson & Lione

(57) ABSTRACT

Gas recirculation systems for use in endoscopic surgical procedures including a gas recirculation pump are disclosed. The gas recirculation pump may work in conjunction with an insufflator used to inflate a patient's peritoneal cavity during surgery. The gas recirculation system may recirculate a high flow rate of gas from and to the patient while filtering particulate matter out of the gas and while maintaining an adequate moisture content in the gas. The gas recirculation pump may include a disposable pump cartridge releasably connected to a pump motor. A controller may detect a fault or safety condition in the gas recirculation system based on the load placed on the pump motor.

18 Claims, 25 Drawing Sheets

(52) U.S. Cl.
CPC . *A61M 2202/0225* (2013.01); *A61M 2205/10* (2013.01); *A61M 2205/125* (2013.01); *A61M 2205/15* (2013.01); *A61M 2205/33* (2013.01); *A61M 2205/3337* (2013.01); *A61M 2205/50* (2013.01); *A61M 2205/502* (2013.01); *A61M 2205/75* (2013.01); *A61M 2209/084* (2013.01); *A61M 2210/1017* (2013.01)

(58) Field of Classification Search
CPC ...... A61M 2205/75; A61M 2210/1017; A61M 2205/33; A61M 2205/502
See application file for complete search history.

(56) References Cited

U.S. PATENT DOCUMENTS

| | | | |
|---|---|---|---|
| 5,507,318 | A | 4/1996 | Israelson |
| 5,836,909 | A | 11/1998 | Cosmescu |
| 5,968,032 | A | 10/1999 | Sleister |
| 6,001,077 | A | 12/1999 | Ellman et al. |
| 6,027,502 | A | 2/2000 | Desai |
| 6,077,246 | A | 6/2000 | Kullas et al. |
| 6,110,259 | A | 8/2000 | Schultz et al. |
| 6,203,590 | B1 | 3/2001 | Byrd et al. |
| 6,299,592 | B1 | 10/2001 | Zander |
| 6,375,653 | B1 | 4/2002 | Desai |
| 6,436,072 | B1 | 8/2002 | Kullas et al. |
| 6,544,210 | B1 | 4/2003 | Trudel et al. |
| 6,589,316 | B1 | 7/2003 | Schultz et al. |
| 6,592,543 | B1 | 7/2003 | Wortrich et al. |
| 6,758,657 | B1 | 7/2004 | McNaull et al. |
| 6,824,139 | B2 | 11/2004 | Barinaga et al. |
| 6,881,236 | B2 | 4/2005 | Schultz et al. |
| 7,083,601 | B1 | 8/2006 | Cosmescu |
| 7,258,712 | B2 | 8/2007 | Schultz et al. |
| 7,273,359 | B2 | 9/2007 | Blight et al. |
| 7,294,116 | B1 | 11/2007 | Ellman et al. |
| 7,311,708 | B2 | 12/2007 | McClurken |
| 7,559,524 | B2 | 7/2009 | Gray et al. |
| 7,597,731 | B2 | 10/2009 | Palmerton et al. |
| 7,766,301 | B2 | 8/2010 | Gray et al. |
| 7,776,014 | B2 | 8/2010 | Visconti et al. |
| 7,789,946 | B2 | 9/2010 | Schultz et al. |
| 7,896,834 | B2 | 3/2011 | Smisson, III et al. |
| 7,959,698 | B2 | 6/2011 | Schultz et al. |
| 8,715,219 | B2 | 5/2014 | Stearns et al. |
| 8,795,232 | B2 | 8/2014 | Visconti et al. |
| 8,961,451 | B2 | 2/2015 | Stearns et al. |
| 9,011,366 | B2 | 4/2015 | Dean et al. |
| 9,039,395 | B2 | 5/2015 | Gray et al. |
| 9,060,678 | B2 | 6/2015 | Larkin et al. |
| 9,115,709 | B2 | 8/2015 | Gray et al. |
| 9,199,047 | B2 | 12/2015 | Stearns et al. |
| 9,283,334 | B2 | 3/2016 | Mantell et al. |
| 10,004,856 | B2 | 6/2018 | Palmerton et al. |
| 2005/0000196 | A1 | 1/2005 | Schultz |
| 2005/0137529 | A1* | 6/2005 | Mantell ............... A61M 13/003 604/129 |
| 2006/0100579 | A1 | 5/2006 | Maahs et al. |
| 2007/0249990 | A1 | 10/2007 | Cosmescu |
| 2014/0260556 | A1 | 9/2014 | Gray et al. |
| 2014/0261704 | A1* | 9/2014 | Hoogenakker ........ G05D 16/00 137/1 |
| 2014/0336567 | A1 | 11/2014 | Stearns et al. |
| 2014/0358070 | A1 | 12/2014 | Stearns et al. |
| 2015/0073346 | A1 | 3/2015 | Visconti et al. |
| 2015/0112246 | A1* | 4/2015 | Palmerton ........... A61M 13/003 604/26 |
| 2015/0125319 | A1 | 5/2015 | Demers et al. |
| 2015/0250939 | A1 | 9/2015 | Kuntz et al. |
| 2015/0290387 | A1 | 10/2015 | Möllstam |
| 2016/0106934 | A1* | 4/2016 | Hiraga .................. A61B 1/015 604/26 |
| 2017/0080167 | A1* | 3/2017 | Surendra ............... A61M 13/00 |

FOREIGN PATENT DOCUMENTS

| | | |
|---|---|---|
| WO | WO 2005/035035 | 4/2005 |
| WO | WO 2008/109014 | 9/2008 |
| WO | WO 2011/041387 | 4/2011 |
| WO | WO2014/038941 | 3/2014 |
| WO | WO 2014/081783 | 5/2014 |
| WO | WO 2015/069182 | 5/2015 |
| WO | WO 2015/150783 | 10/2015 |
| WO | WO 2015/174861 | 11/2015 |

OTHER PUBLICATIONS

Kyle J. Weld, et al. "Analysis of Surgical Smoke Produced by Various Energy-Based Instruments and Effect on Laparoscopic Visibility", Journal of Endourology, Mar. 2007, 6 pgs.

W.L. Barrett, et al., "Surgical Smoke—a review of the literature, Is this just a lot of hot air?", Surg Endosc; Apr. 25, 2002, 9 pgs.

U.S. Appl. No. 62/037,893 filed Aug. 15, 2014.

International Search Report and Written Opinion for corresponding application No. PCT/US2016/040642 dated Oct. 12, 2016 (9 pgs).

Examination Report for Singapore Application No. 11201710831Q dated Jun. 13, 2019.

* cited by examiner

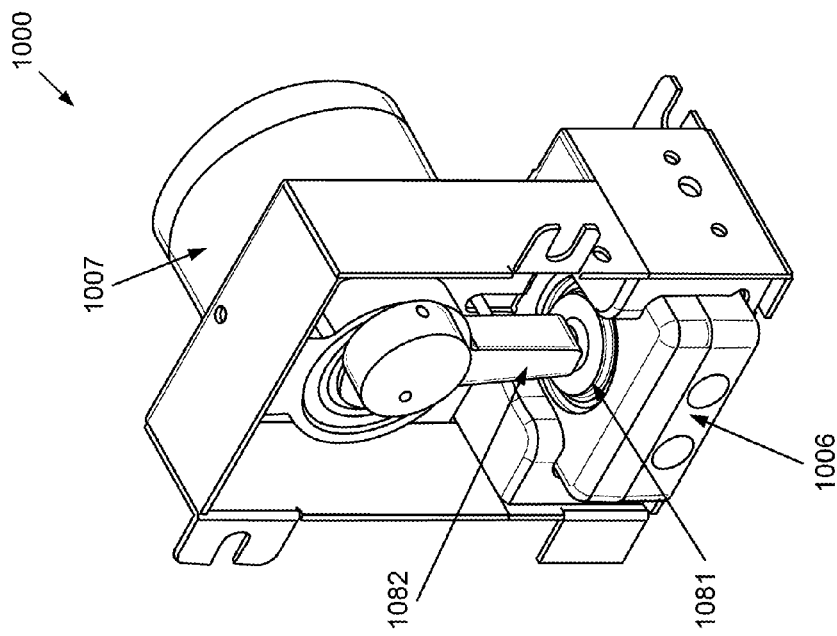
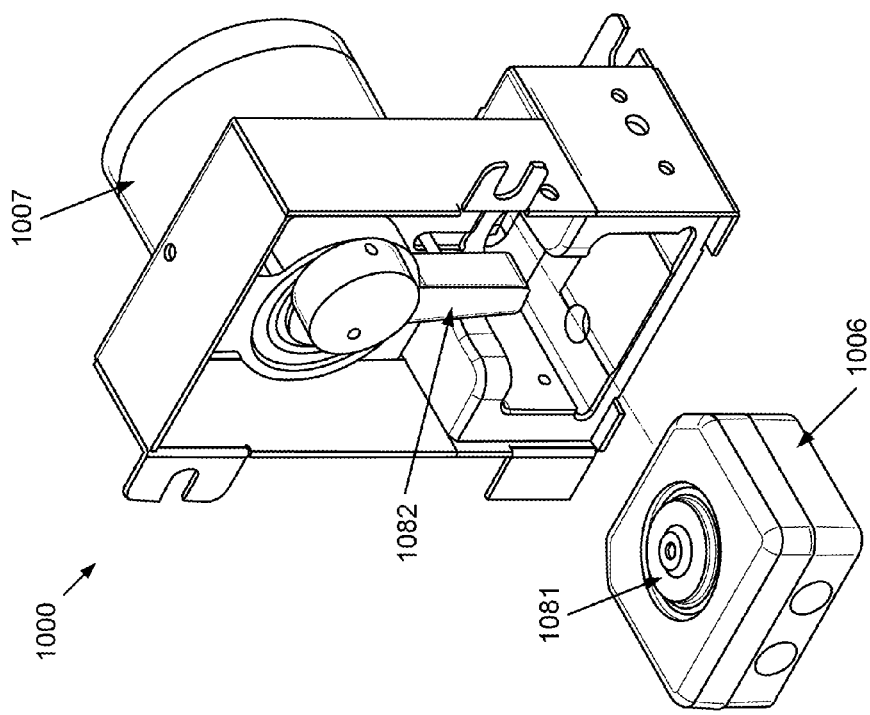

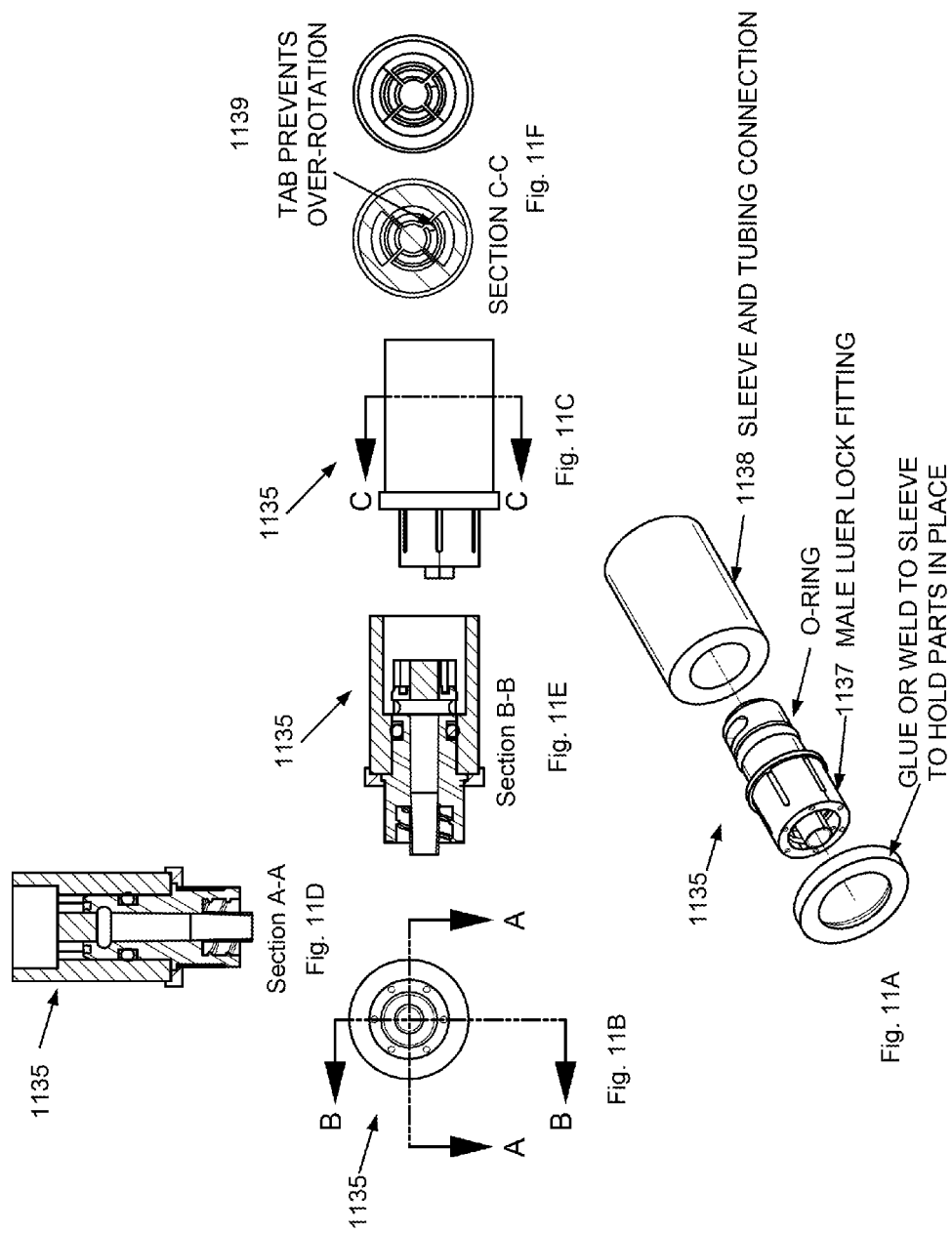

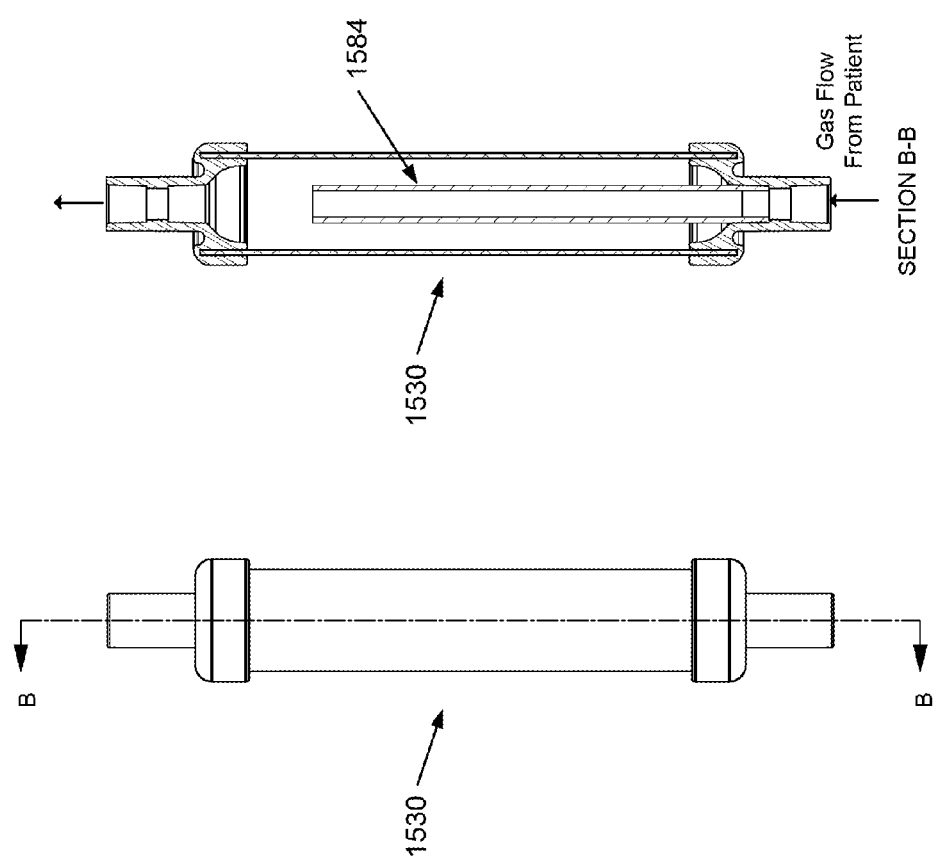

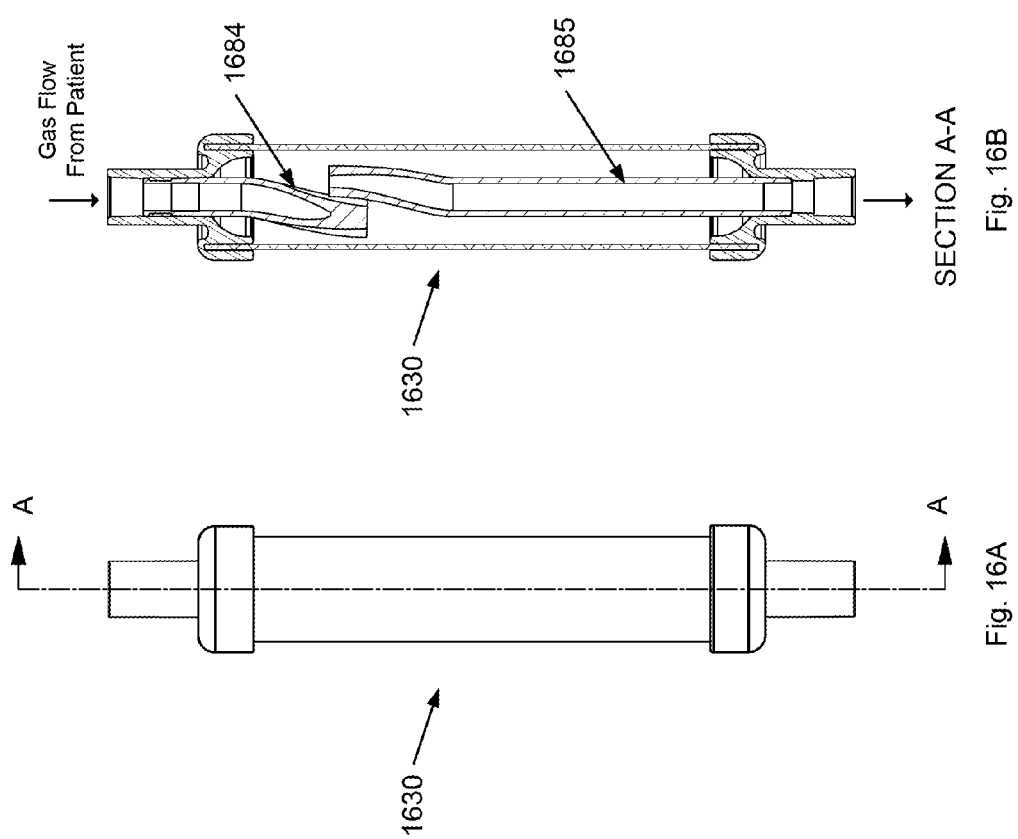

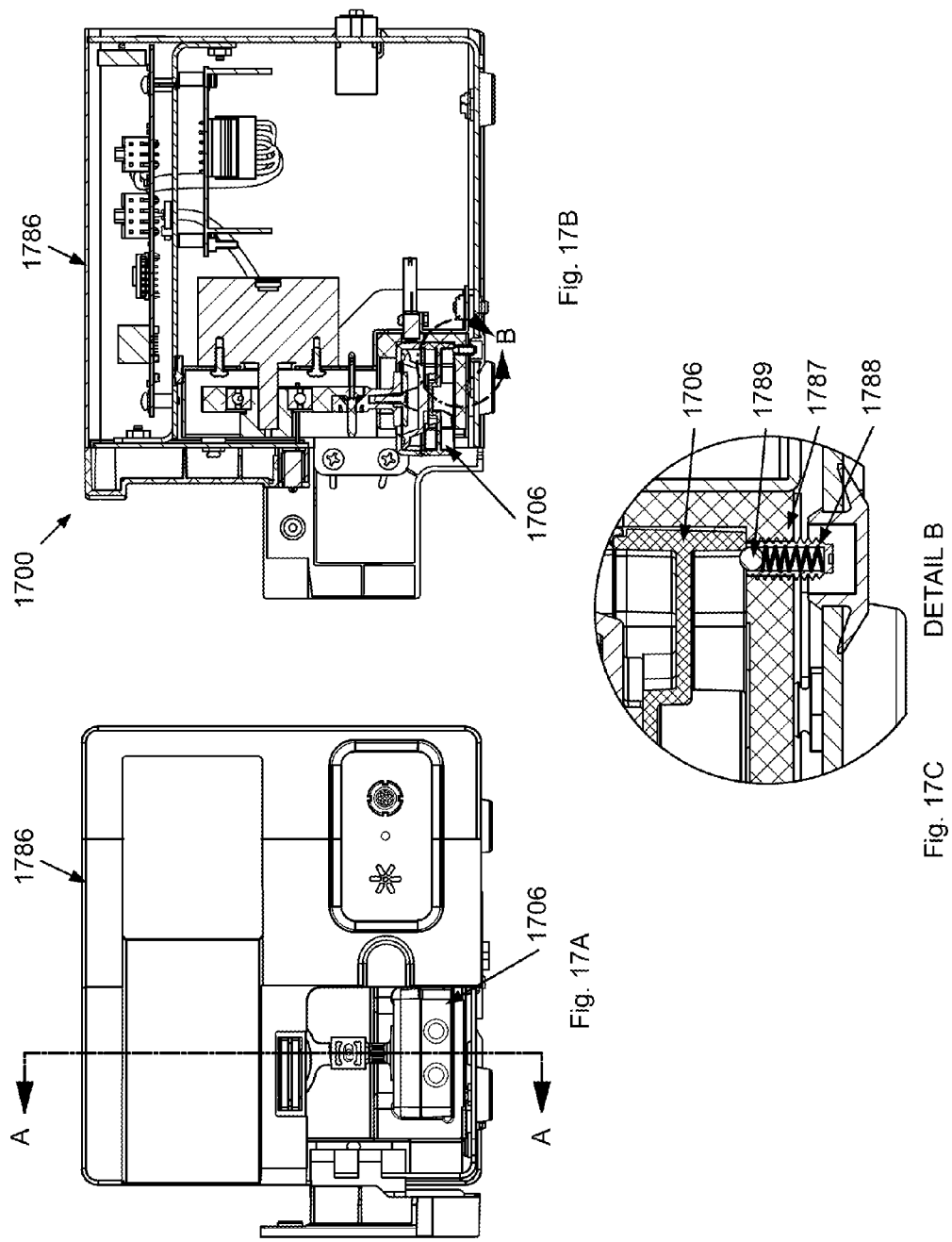

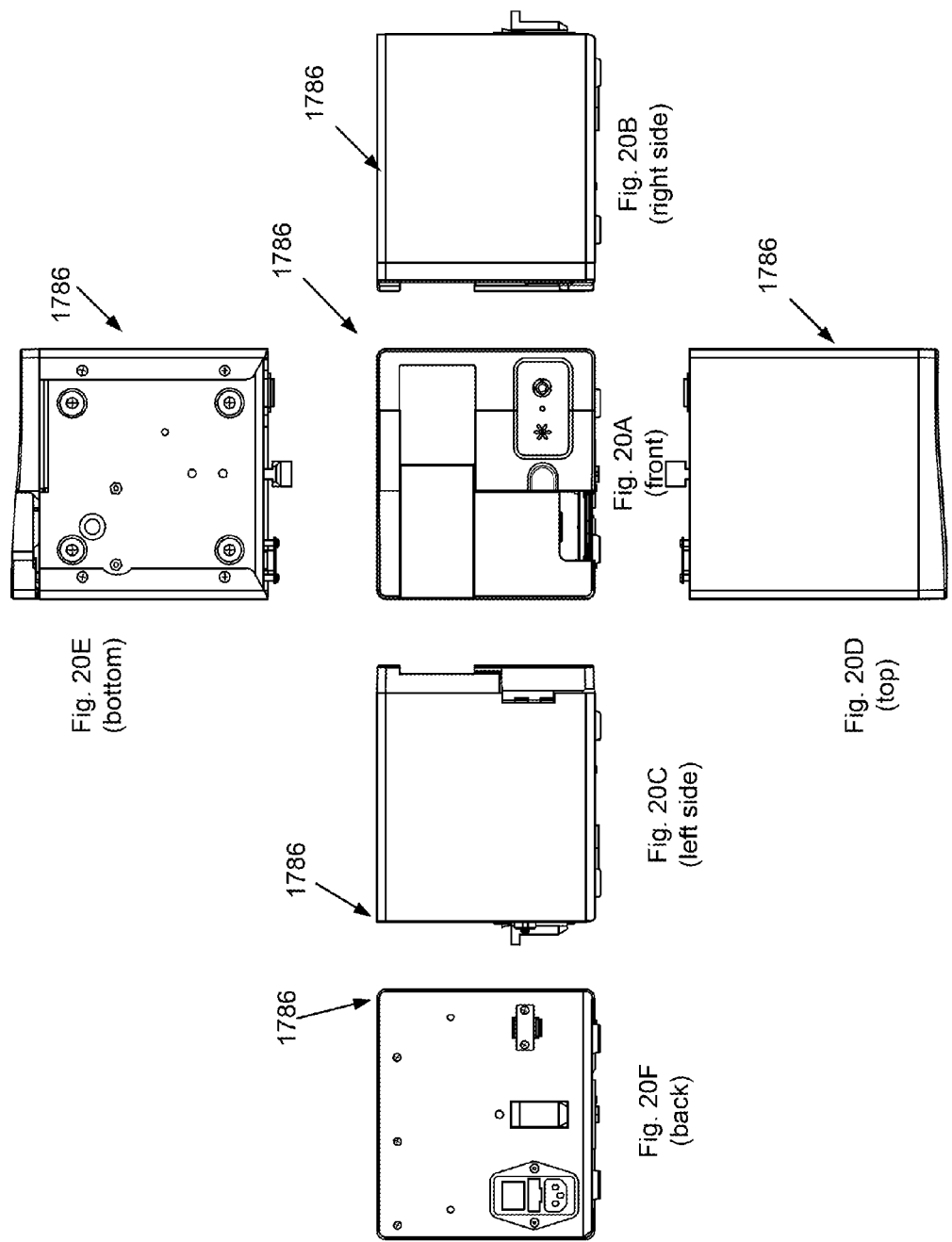

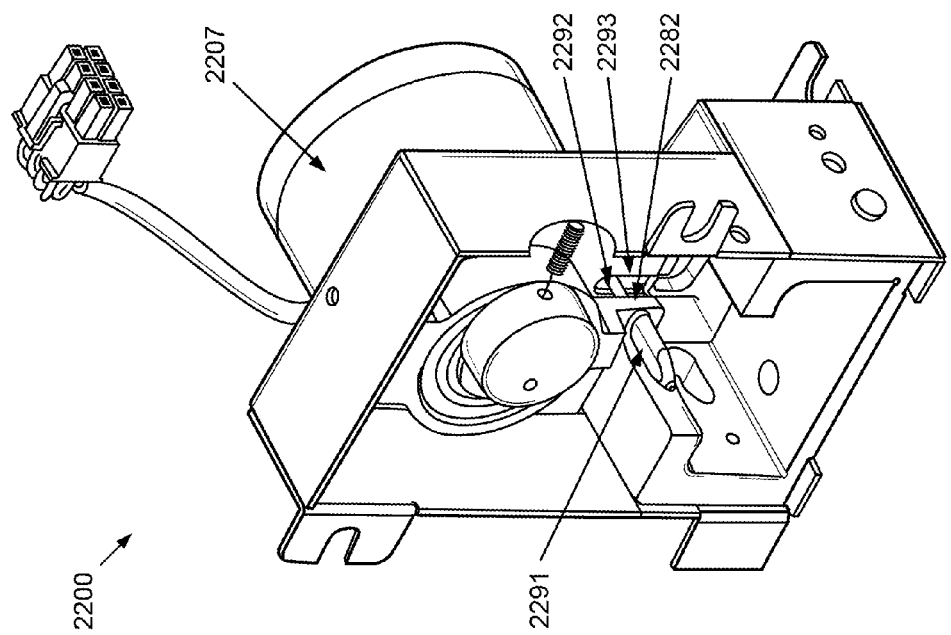
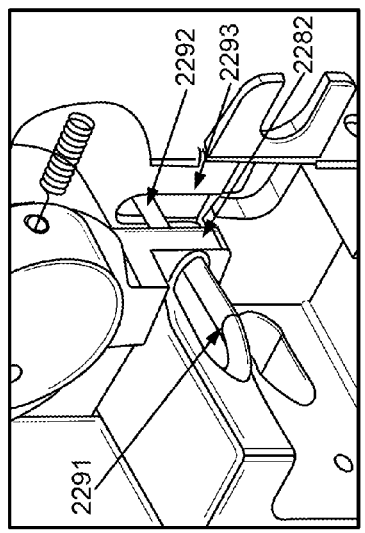

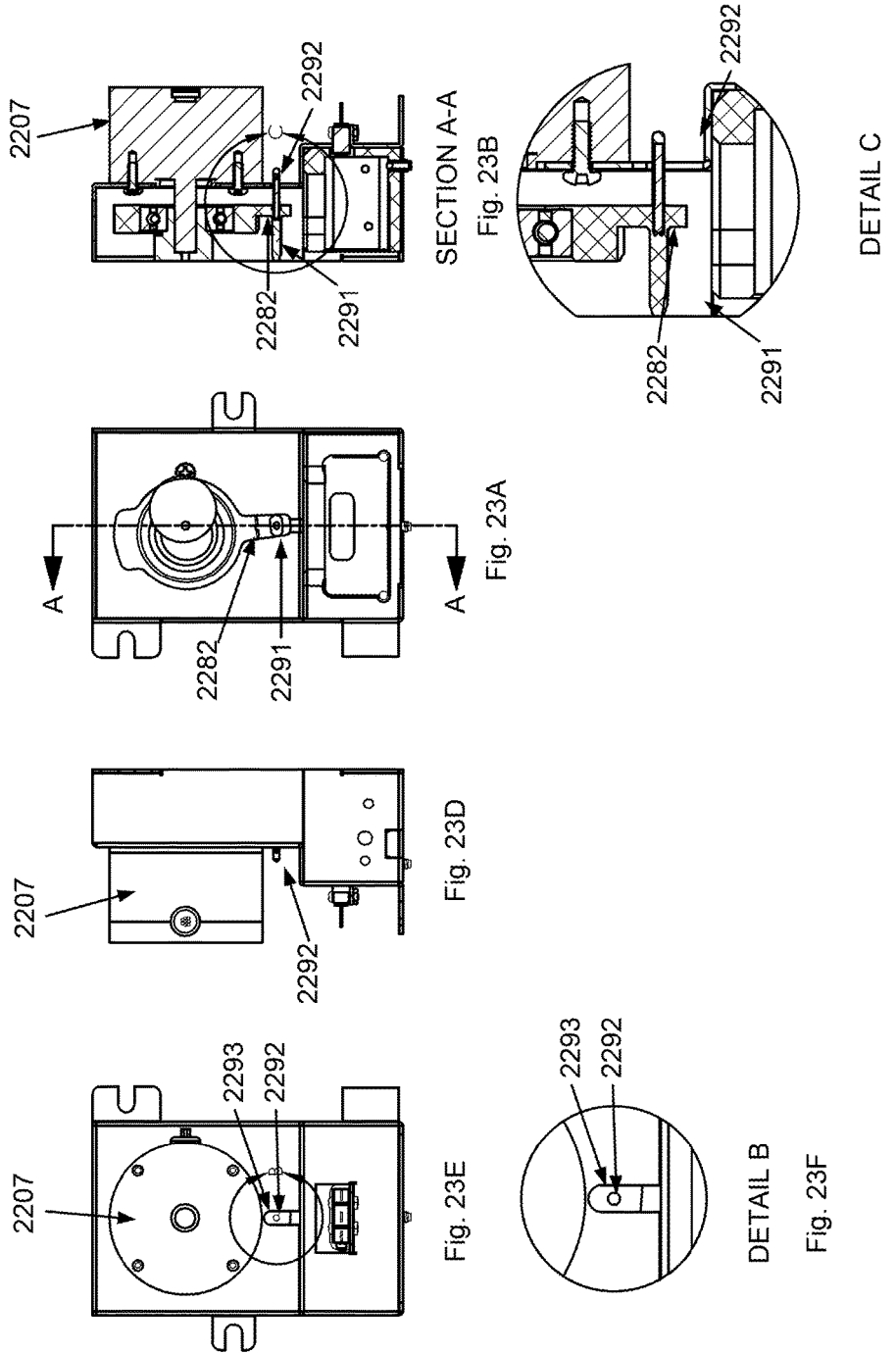

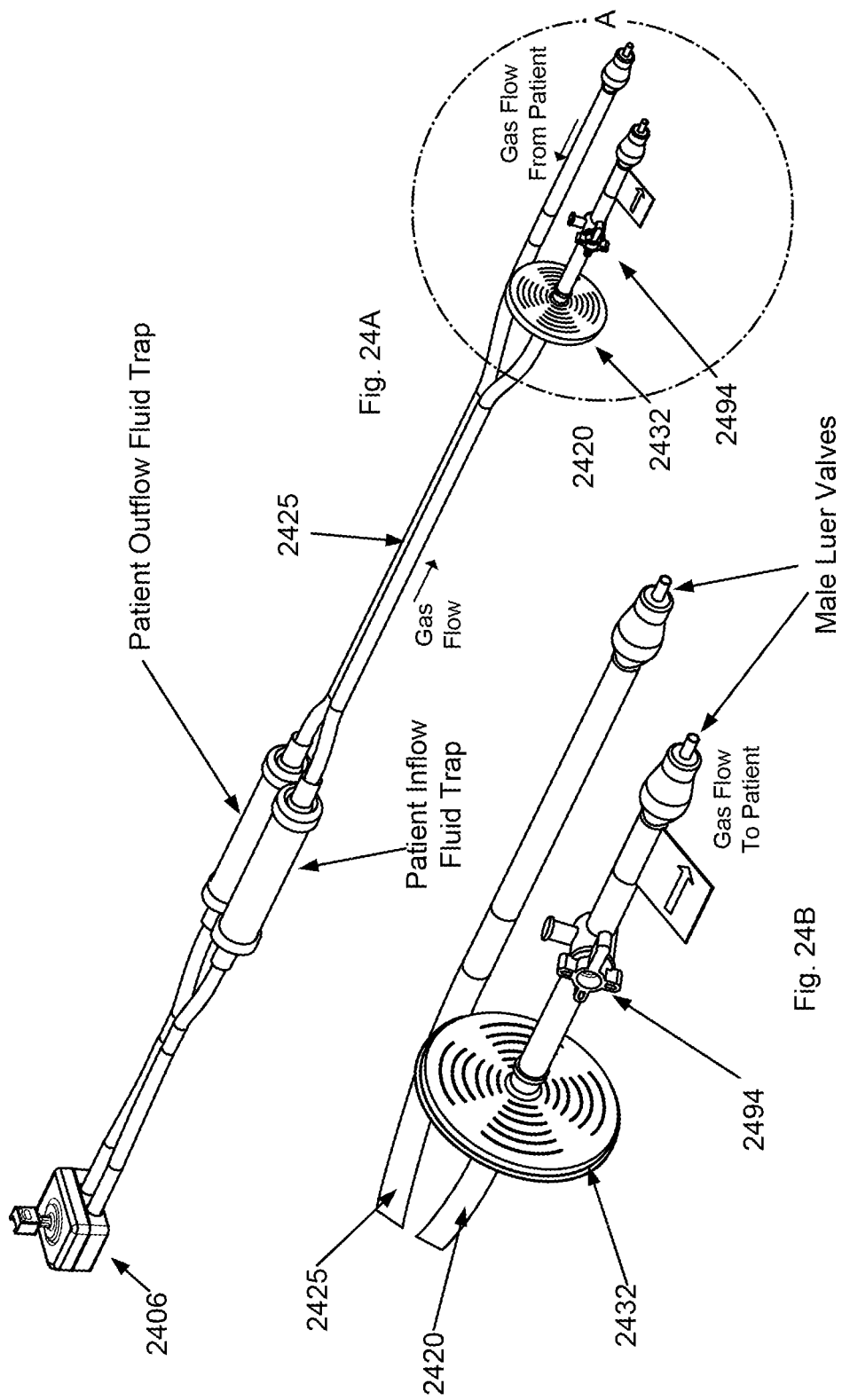

GAS RECIRCULATION SYSTEM AND METHOD

CROSS-REFERENCE TO RELATED APPLICATION

This application claims benefit of U.S. Provisional Patent Application Ser. No. 62/188,319, filed Jul. 2, 2015.

BACKGROUND

1. Technical Field text

The present disclosure relates to gas recirculation systems used in minimally invasive surgical procedures.

2. Background Information

Minimally invasive surgical procedures, including endoscopic surgical procedures, such as laparoscopic, arthroscopic, hyteroscopic, thoracoscopic surgical procedures, are becoming more common place in the surgical environment due to shorter recovery times, shorter operating durations, and reduced costs. Minimally invasive surgical procedures are typically performed with instruments inserted through small, artificially created openings or portals in the patient.

In a laparoscopic surgical procedure, a gas is injected into the peritoneal cavity through an artificial opening in the abdomen created by a verres needle. Typically, the type of gas that is injected is a $CO_2$ gas, although a mixture of two or more gases or a different gas may also be suitable depending on the surgical procedure. In a laparoscopic procedure, the $CO_2$ gas is used to distend the pneumoperitoneum, thereby creating an air space for the surgeon to visualize the organs and to maneuver surgical instruments and an endoscope. The $CO_2$ gas is injected into the peritoneal cavity under pressure by an insufflation device. Examples of insufflation devices suitable for this application are described in U.S. Pat. No. 6,299,592 and U.S. Patent Ser. No. 62/037,893, which are all hereby incorporated by reference.

After the pneumoperitoneum is first distended, an endoscope with a camera (which is connected to a monitor) is inserted into the abdominal cavity to visualize the interior of the cavity and, more particularly, the operative space. The endoscope typically remains inserted for the duration of the surgical procedure. Other openings may also be created to provide access to other surgical instruments into the abdominal cavity.

The instrumentation used to cut, cauterize, ablate or vaporize tissues inside the abdomen during a minimally invasive surgical procedure, such as a laparoscopic procedure, results in surgical smoke which may pose a health risk to the patient and may also pose a health risk to the surgeon and other individuals in the operating room if some or all of the surgical smoke escapes to the operating room. As used herein, the term "surgical smoke" includes, without limitation, gases or aerosols that may contain toxins, particulate matter, irritants, viable cells and viruses, water vapor, and other contaminants. Surgical smoke also impairs the surgeon's visualization via the camera in the endoscope. This impairment to visualization can also be further accentuated by fogging or condensation on the camera lens due to the $CO_2$ gas entering the abdominal cavity at below body temperature. Impairing visualization can interfere with the surgical procedure and result in risk to the patient's health. Furthermore, impairing visualization may also lead to delays in the operation, in particular in operations involving robotic assisted surgical procedures performed remotely.

BRIEF SUMMARY

In one aspect, a gas recirculation system for use in an endoscopic surgical procedure comprises a pump with a motor and a pump cartridge coupled to the motor. The pump cartridge includes a gas input connection and a gas output connection. The pump cartridge is detachable from the motor and the pump cartridge is sealed such that a gas within the pump cartridge cannot contact the motor. The gas recirculation system also comprises a first and second tube in fluid communication with the gas input and gas output connections, respectively. The first and second tubes are configured to be connectable to surgical equipment that is insertable into a peritoneal cavity. The pump is configured to draw gas into the gas input connection from a peritoneal cavity through the first tube and to discharge gas out of the gas output connection and into a peritoneal cavity through the second tube Other systems, methods, features and advantages will be, or will become, apparent to one with skill in the art upon examination of the following figures and detailed description. It is intended that all such additional systems, methods, features and advantages be included within this description, be within the scope of the invention, and be protected by the following claims.

BRIEF DESCRIPTION OF THE DRAWINGS

FIGS. 10A and 10B are an example of an embodiment of a coupling method between a gas recirculation pump cartridge and a motor.

FIGS. 11A-11F are an example of an embodiment of a connecting element used in a gas recirculation system.

FIGS. 15A and 15B are an example of an embodiment of a moisture trap used in a gas recirculation system.

FIGS. 16A and 16B are an example of another embodiment of a moisture trap used in a gas recirculation system.

FIGS. 17A-17C are an example of an embodiment of an enclosure for a gas recirculation system.

FIGS. 20A-20F are an example of another embodiment of an enclosure for a gas recirculation system.

FIGS. 22A and 22B are an example of another embodiment of a coupling method between a gas recirculation pump cartridge and a motor.

FIGS. 23A-23F are an example of another embodiment of a coupling method between a gas recirculation pump cartridge and a motor.

FIGS. 24A and 24B are an example of an embodiment of a three-way valve used in a gas recirculation system.

DETAILED DESCRIPTION

The present disclosure is directed to a system for recirculating gas injected into a peritoneal cavity during a surgical procedure. The system includes a positive displacement pump to remove and inject gas into the peritoneal cavity in order to remove smoke generated within the peritoneal cavity during the surgical procedure.

The present disclosure provides a safe, cost effective gas recirculation system with component parts that can be reused without sterilization. The cost effective system utilizes controllers, rather than sensors, to monitor the pump operation and detect faults. The system is able to achieve high removal and injection flow rates, for example 4 to 10 liters per minute, which ensures that any surgical smoke is quickly and effectively removed from the surgeon's field of vision while at the same time minimizing any change in pressure in the peritoneal cavity.

Figure 1:
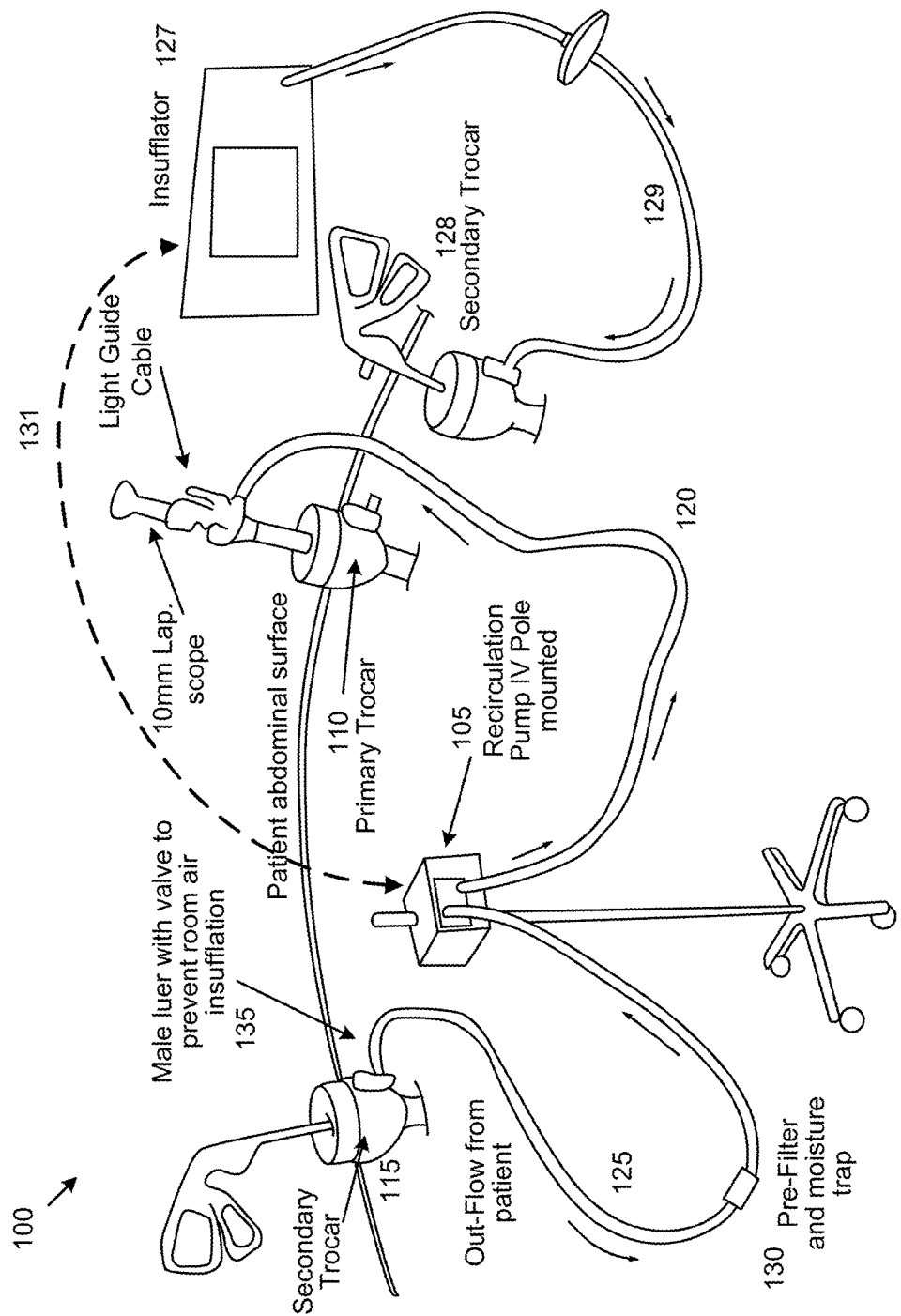
FIG. 1 is an illustrative example of an embodiment of a gas recirculation system.

Referring to FIG. 1, an embodiment of a gas recirculation system 100 is shown. Gas recirculation system 100 may include a recirculation pump 105, a primary input trocar 110, a secondary output trocar 115, input tubing 120, and output tubing 125. Output tubing 125 may include a filter and/or moisture trap 130. Input tubing 120 and output tubing 125 may be similar to insufflation tubing sets manufactured by Northgate Technologies.

Gas recirculation system 100 may be used in conjunction with an insufflation system, such as described in U.S. Pat. No. 6,299,592 and U.S. Patent Ser. No. 62/037,893, which are all hereby incorporated by reference. The insufflation system may include an insufflator 127, an insufflation trocar 128, insufflation tubing 129 connecting the insufflator 127 to the insufflation trocar 128, and an electronic communication line 131 between gas recirculation system 100 and insufflator 127. Gas recirculation system 100 may include a controller to communicate with insufflator 127 through communication line 131. Information or commands such as start, stop, flow increase, flow decrease, or other functions of the gas recirculation controller could reside in insufflator 127 and communicated to the gas recirculation controller. Additionally or alternatively, the gas recirculation controller could be integrated into and shared with insufflator 127. The gas recirculation system 100 and insufflator 127 may share power supplies, processors, graphic user interfaces, heat functions, humidity functions, to name a few examples.

Recirculation pump 105 removes gas from the patient through secondary output trocar 115, output tubing 125, and filter/moisture trap 130. A valve 135 may connect secondary output trocar 115 to output tubing 125. When output tubing 125 is connected to secondary output trocar 115 through valve 135, the valve stem of valve 135 may be deflected to an open position. When valve 135 is disconnected from secondary output trocar 115, the valve stem of valve 135 may return to its natural closed position. Valve 135 may allow gas to flow through the valve when output tubing 125 is connected to secondary output trocar 115. Valve 135 may prevent gas from entering output tubing 125 when output tubing 125 is disconnected from secondary output trocar 115. Valve 135 may automatically close when output tubing 125 is disconnected from secondary output trocar 115. Valve 135 may be a luer valve, such as a Texium® or Halkey/Roberts® brand of closed male luers.

Recirculation pump 105 also injects gas into the patient through primary input trocar 110 and input tubing 120. A valve, similar to valve 135, may connect primary input trocar 110 and input tubing 120 and may close when input tubing 120 is disconnected from primary input trocar 110.

Recirculation pump 105 recirculates gas from the peritoneal cavity, through filter/moisture trap 130, and back into the peritoneal cavity. The flow rate of gas removed from the patient through output tubing 125 is the same as or substantially similar to the flow rate of gas injected back into the patient through input tubing 120. Filter/moisture trap 130 may remove liquid from the gas and may remove particulate from the gas, such as surgical smoke particles. Filter/moisture trap 130 may include a media that readily absorbs liquid, preferably up to 15 to 20 ml of liquid, and readily releases moisture into the gas flowing over or through the media. A media that is suitable for use includes the Crystar® brand of material. The size of the media is preferably 1-2.5 inches long and 0.5-2.0 inches in diameter and most preferably 1.5-2.0 inches long and 1-1.5 inches in diameter. In one embodiment, the media may have a serrated outer surface and a center opening. When placed in a filter housing, the serrated outer surface defines a plurality of channel openings in which the gas can flow and the center opening may be filled with a rod comprising charcoal. The charcoal may entrap particulate matter in the gas as it passes through the center opening and at the same time may be effective at removing undesirable odor from the gas. Additionally or alternatively, odor removal can be accomplished using other materials, such as enzymatic materials, vinegar and water cartridges, or odor can be masked using fragrances. Filter/moisture trap 130 may allow the gas that is recirculated to retain moisture in a range of 50-70% relative humidity. Preferably, the gas recirculation system 100 will allow for the recirculation of gas to and from the patient and will passively maintain a humidity level of the gas that will be a minimum of 70% relative humidity with the gas at normal operating room temperatures between 60-75 degrees Fahrenheit. Utilizing gas recirculation system 100 may reduce or eliminate the need for insufflator 127 to inject additional $CO_2$ gas in the peritoneal cavity and may also maintain a reasonable moisture level in the peritoneal cavity, as opposed to added $CO_2$ which, unless it first passes through a gas warmer humidifier (an additional cost) will be very dry, typically at 0% relative humidity. The recirculation of gas will not only reduce the input of 0% relative humidity gas, but also may prevent the breathing effect caused by insufflator 127 attempting to maintain pressure in the peritoneal cavity, and prevent the discharge of large amounts of $CO_2$ gas into the operating room. For example, passive smoke removal systems that allow six liter per minute leak rates may discharge up to 270 liters of $CO_2$ gas into the operating room during a normal 45 minute gall bladder procedure. Accordingly, gas recirculation system 100 is a cost effective method to maintain adequate humidity of gas in the peritoneal cavity.

Figure 2:
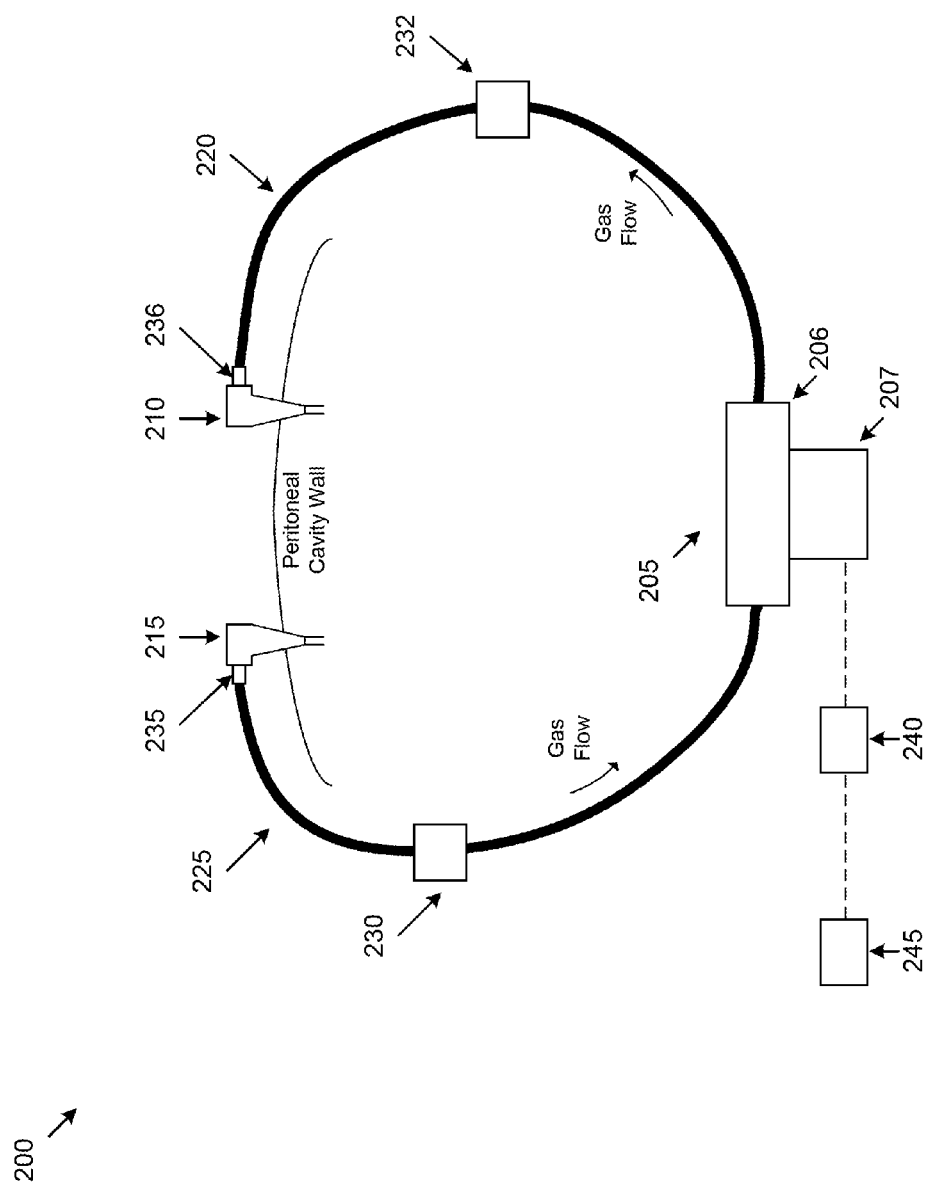
FIG. 2 is a schematic example of an embodiment of a gas recirculation system.

Referring to FIG. 2, an embodiment of a gas recirculation system 200 is shown. Gas recirculation system 200 may include some of the same components and operational characteristics as gas recirculation system 100. Gas recirculation system 200 may include a recirculation pump 205, an input trocar 210, an output trocar 215, input tubing 220, and output tubing 225. Output tubing 225 may include a filter and/or fluid trap 230. Input tubing 220 may include a filter 232. A valve 235 may connect output trocar 215 to output tubing 225. A valve 236 may connect input trocar 210 to input tubing 220. Valves 235, 236 may operate with the same characteristics, such as automatically closing when disconnected, and in the same manner as valve 135.

Recirculation pump 205 may be a diaphragm pump, or any other suitable positive displacement pump, including a cartridge 206 and a motor 207. Cartridge 206 may be disconnectable from motor 207. Motor 207 may be any type of motor. Motor 207 may preferably be, but not limited to, a direct current ("DC") motor. Cartridge 206 may be sealed to prevent gas from escaping cartridge 206 except through the connection to input tubing 220 and outlet tubing 225. Cartridge 206 may be composed of multiple components that are attached to one another, such as by ultrasonic welding, using adhesives, laser welding, mechanical snapping connection with or without a gasket, or any other known method of combining and sealing mating surfaces together. Cartridge 206 may be sealed so that it is only in fluid communication with the opening to inlet tubing 220 and outlet tubing 225. Accordingly, gas within cartridge 206 may not come in contact with motor 207 or other parts of recirculation pump 205. The gas recirculation system may be an inexpensive method to remove surgical smoke from a patient's peritoneal cavity because motor 207 is not contaminated from contact with gas from the peritoneal cavity, and therefore, can be reused without requiring sterilization. The portions of recirculation pump 205 that may have been contaminated from contact with gas from the peritoneal cavity, such as cartridge 206, may be disposable.

When in operation, the gas recirculation system 200 may remove gas, including surgical smoke, from a peritoneal cavity preferably at a flow rate of 4-10 liters per minute and most preferably at a flow rate of 6-8 liters per minute and, after filtration, inject it back into the peritoneal cavity preferably at a flow rate of 4-10 liters per minute and most preferably at a flow rate of 6-8 liters per minute. The gas from the peritoneal cavity first travels through output trocar 215, through valve 235, and into output tubing 225. The gas may travel through fluid trap 230 which may remove condensate/liquid that forms due to the change in temperature of the gas (i.e. from body temperature to room temperature) and odor if a charcoal rod, (as described above) or a separate or integrated activated charcoal filter is used. The gas then travels through cartridge 206 of recirculation pump 205. The gas may travel through a filter that is located before or after recirculation pump 205, such as filters 230 or 232. The filter may remove particulate matter and other contaminants from the gas. The filter is preferably is made of a material that provides a pressure drop of no more than 12.3 mmHG at a 20 liter per minute flow rate. The gas may be injected back into the peritoneal cavity through input tubing 220, valve 236, and input trocar 210.

Recirculation system 200 may include controller 240 to control the operation of motor 207. Controller 240 may be combined with or used in conjunction with an insufflator connected to recirculation system 200. Controller 240 may be the Tiva® (Texas Instruments) brand of controllers. Controller 240 may be used to detect operating and fault conditions of motor 207 and/or safety issues in gas recirculation system 200. Controller 240 may detect the amount of power drawn by motor 207, such as by measuring the voltage to motor 207. Controller 240 may detect or determine that a fault or safety issue has occurred in gas recirculation system 200 based on the amount of power drawn by motor 207. For example, controller 240 may determine a fault condition or safety issue occurs if motor 207 draws more power than expected, as measured by an increase in voltage or current greater than a predetermined amount. Controller 240 may trigger a shutdown of motor 207 if a fault condition or safety issue occurs. Using controller 240 to detect fault conditions or safety issues in gas recirculation system 200 may be more cost effective than using sensors.

Valves 235 and 236 may be configured to close if they are disconnected from output trocar 215 and input trocar 210, respectively. Closing valve 235 when it is disconnected from output trocar 215 may restrict entrainment of ambient air into the suction side of gas recirculation system 200. Any ambient air entrained in gas recirculation system 200 would be injected into the peritoneal cavity by recirculation pump 205. Closing valve 236 when it is disconnected from input trocar 210 may prevent discharging gas from the peritoneal cavity into the ambient environment.

Closing valves 235 or 236 may create a pressure differential in the gas circuit of gas recirculation system 200. A pressure differential may increase the load on motor 207, as measured by an increase in voltage or current drawn by motor 207. If the increase in voltage or current is above a predetermined threshold value, controller 240 may detect a fault condition or safety issue in gas recirculation system 200. Controller 240 may trigger a shutdown of motor 207 upon detection of a fault condition or safety issue in gas recirculation system 200. For example, valve 235 will close if valve 235 and output tubing 225 are disconnected from output trocar 215. Closing valve 235 will cause recirculation pump 205 to pull suction on a closed tube, which will force recirculation pump 205 to work harder and motor 207 to draw more power in order to maintain its proper speed. The increase in power drawn by motor 207 may result in a fault condition if the voltage or current increase is above a predetermined value. Upon detection of the fault condition caused by disconnecting valve 235 from output trocar 215, controller 240 may trigger recirculation pump 205 to shut down. Similarly, valve 236 will close if valve 236 and input tubing 220 are disconnected from input trocar 210. Closing valve 236 will cause recirculation pump 205 to pump against a closed tube or "dead head," which will force recirculation pump 205 to work harder and motor 207 to draw more power in order to maintain its proper speed. The increase in power drawn by motor 207 may result in a fault condition if the voltage or current increase is above a predetermined value. Upon detection of the fault condition caused by disconnecting valve 236 from input trocar 210, controller 240 may trigger recirculation pump 205 to shut down. Accordingly, gas recirculation system 200 may monitor the status of output tubing 225 and input tubing 220 by using controller 240 to monitor motor 207.

In a similar manner, gas recirculation system 200 may monitor the connection status of input trocar 210 and output trocar 215 with the peritoneal cavity. Removing input trocar 210 or output trocar 215 from the peritoneal cavity will affect the operation of recirculation pump 205 and motor 207 by changing the pressure of the suction source or discharge source of recirculation pump. Controller 240 may detect the change in operation of the motor 207 and determine that input trocar 210 or output trocar 215 has been removed from the peritoneal cavity. For example, removing input trocar 210 from the peritoneal cavity would decrease the power required for motor 207 to maintain the same speed because recirculation pump 205 would no longer be pumping to overcome the intraperitoneal pressure. Controller 240 may detect the decreased power drawn by motor 207 and determine that input trocar 210 has been disconnected from the peritoneal cavity. Controller 240 may then trigger recirculation pump 205 to shutdown to prevent gas from the peritoneal cavity entering the ambient environment.

Gas recirculation system 200 may include a user interface 245, such as a computer, to allow an operator to determine or confirm the status of gas recirculation system 200. For example, if controller 240 shuts down recirculation pump 205 because valve 235 is disconnected from output trocar 215, user interface 245 may display that recirculation pump 205 is shut down and that the likely cause is output tubing 225 being disconnected from output trocar 215. An operator may confirm that output tubing 225 is disconnected from output trocar 215 and reconnect it in order to restart recirculation pump 205. Similarly, an operator may determine if other fault conditions have occurred, such as blockage, excessive restriction in the gas path, or a leakage in the gas path, such as disconnected or damaged tubing.

Figure 3:
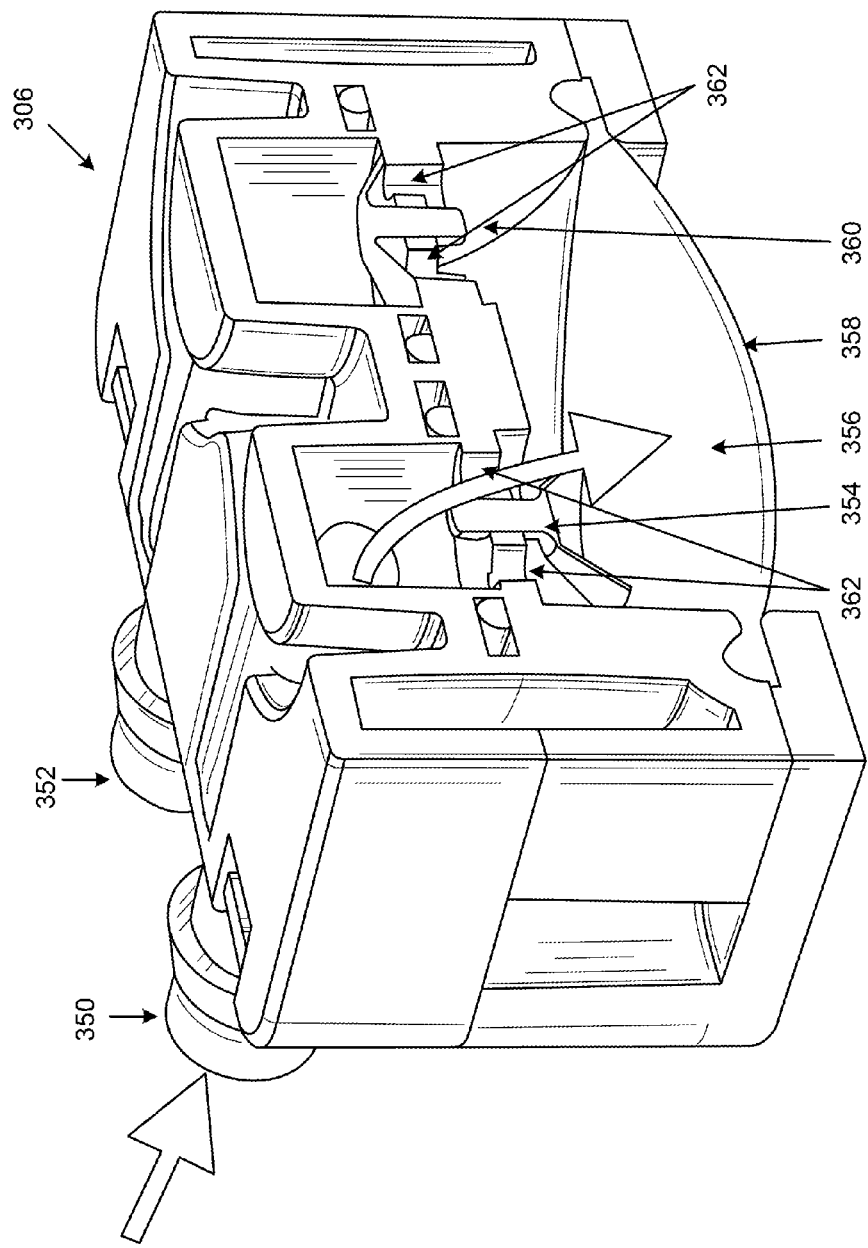
FIG. 3 is an example cross-section of an embodiment of a gas recirculation pump cartridge.
Figure 4:
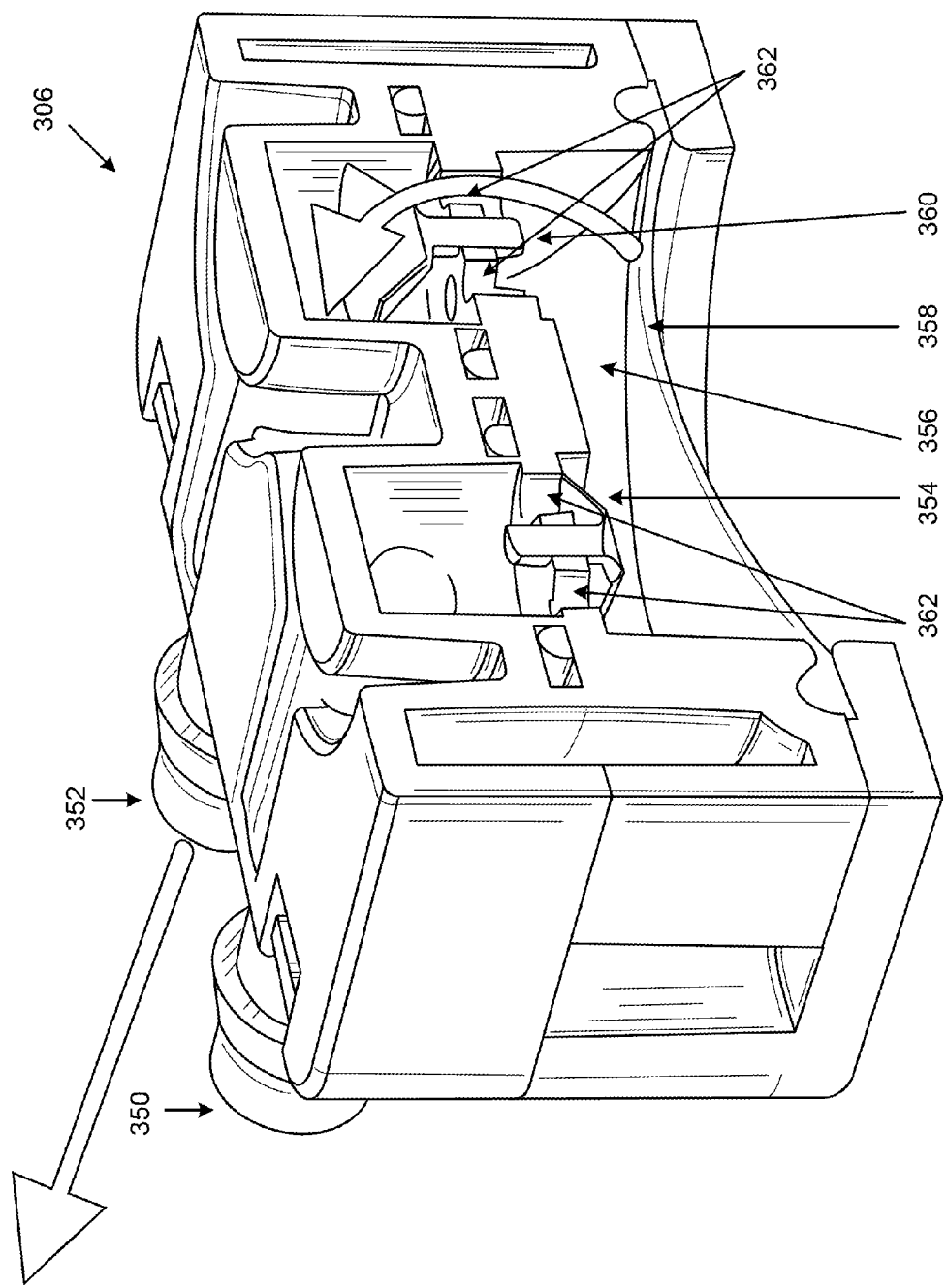
FIG. 4 is another example cross-section of an embodiment of a gas recirculation pump cartridge.
Figure 5:
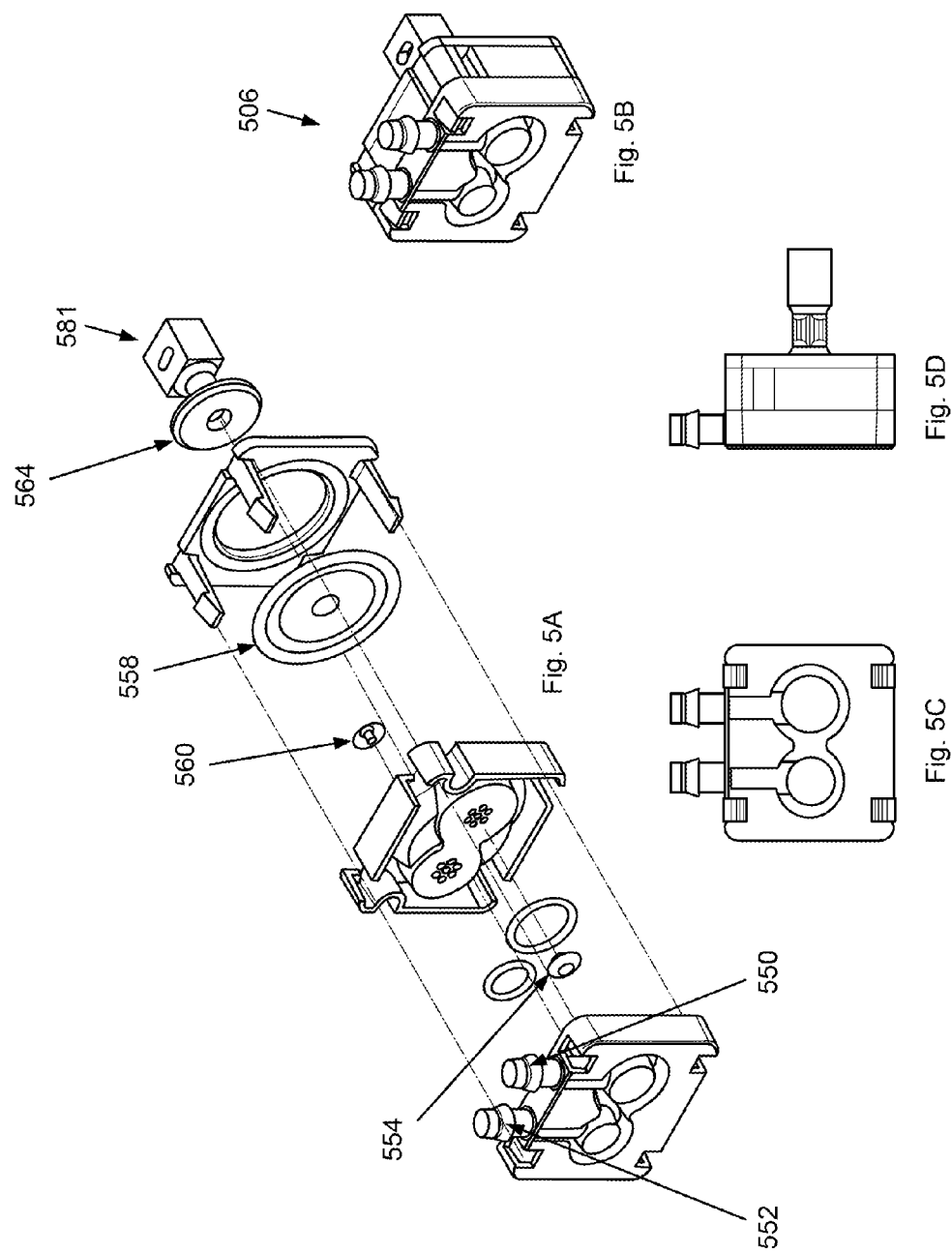
FIGS. 5A-5D are an example of an embodiment of a gas recirculation pump cartridge.
Figure 6:
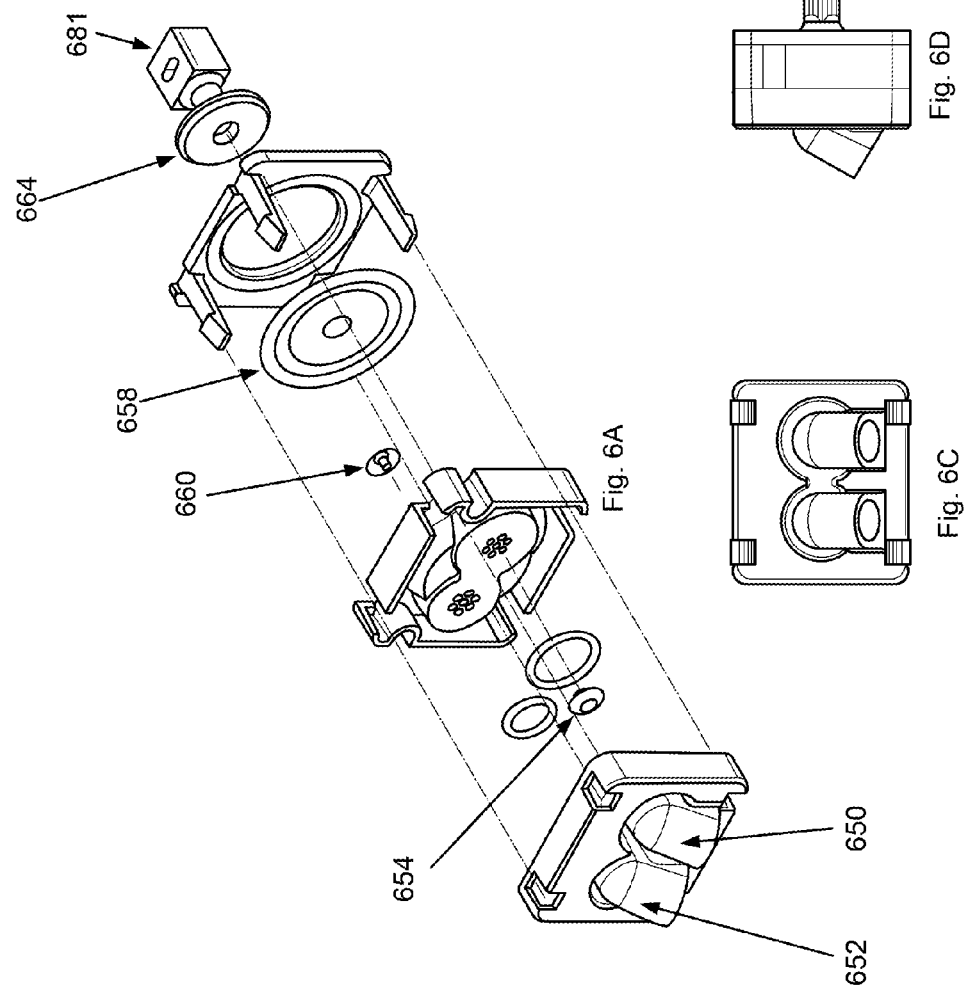
FIGS. 6A-6D are another example of an embodiment of a gas recirculation pump cartridge.
Figure 7:
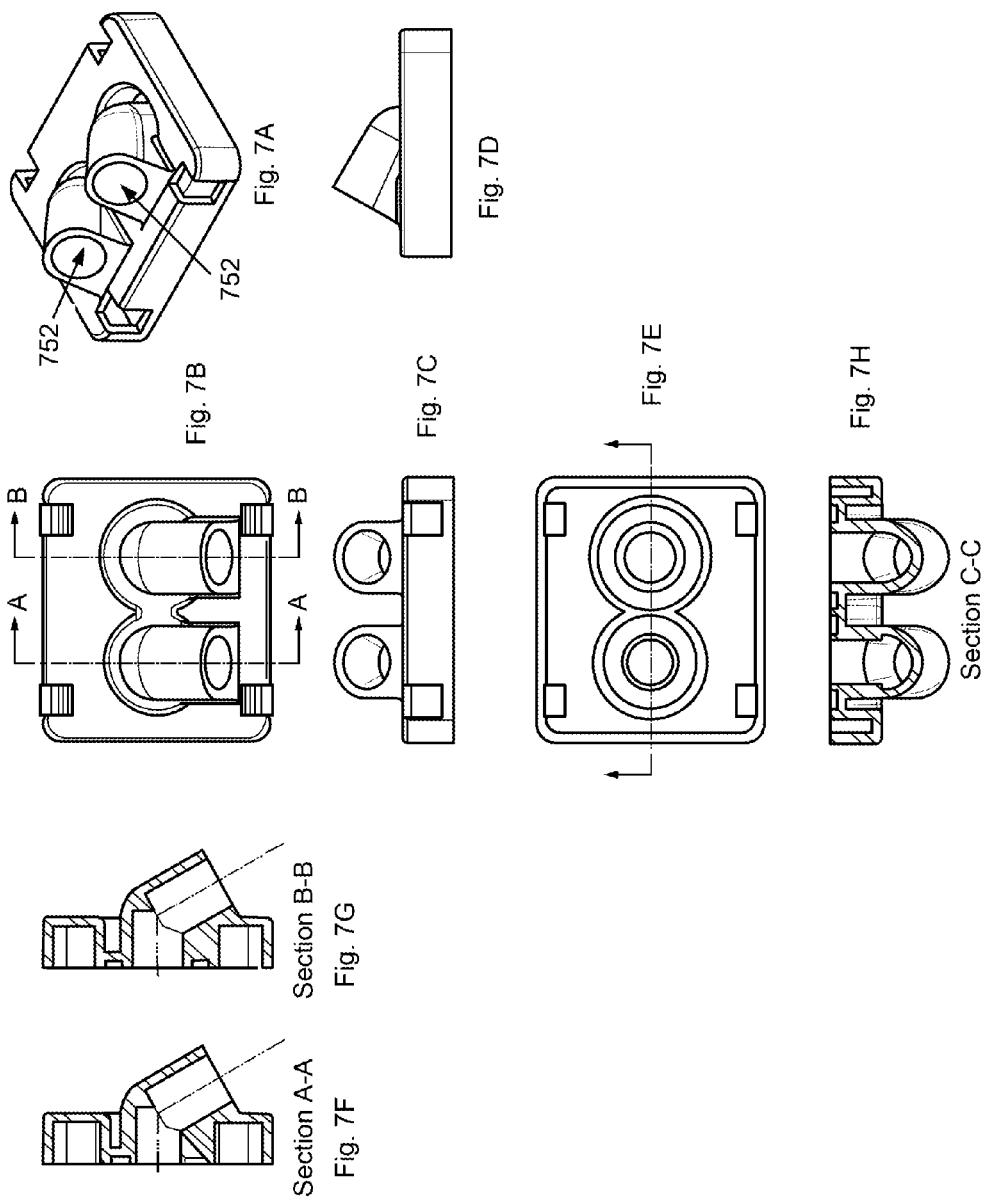
FIGS. 7A-7H are an example of an embodiment of a portion of a gas recirculation pump cartridge.

Referring to FIG. 3 and FIG. 4, an embodiment of a cartridge 306 used in a recirculation pump is shown. Cartridge 306 may be used in a recirculation pump such as recirculation pump 205 described in relation to FIG. 2. FIG. 3 and FIG. 4 show a partial cross-sectional view of cartridge 306. Arrows showing the gas flow path are included in order to better describe the operation of cartridge 306. Cartridge 306 includes connection 350 to output tubing, such as output tubing 225 in FIG. 2, that may be connected to a peritoneal cavity. Cartridge 306 includes connection 352 to input tubing, such as input tubing 220 in FIG. 2, that may be connected to a peritoneal cavity.

Gas from the peritoneal cavity enters cartridge 306 through connection 350, as shown by the arrow in FIG. 3. Cartridge 306 may include valves 354 and 360. The gas travels into cartridge 306 through valve 354 into diaphragm chamber 356, as shown by the arrow in FIG. 3. The gas travels out of cartridge 306 from diaphragm chamber 356 through valve 360, as shown by the arrow in FIG. 4 (discussed below). Valves 354 and 360 may be umbrella valves. The diameter of the gas opening 362 through valves 354 and 360 may be between 0.05 inches and 0.15 inches and may be preferably a diameter of 0.085 inches. The gas openings 362 may include more than one concentric opening, such that the combined area of the gas openings 362 may be sized to permit flow rates within a range of 4 liters per minute up to 10 liters per minute and a preferred range of 7 to 8 liters per minute. Although flow rates of 4-10 liters per minute are an acceptable flow range, higher or lower flow rates can be achieved by enlarging or reducing the size of the cartridge, increasing or decreasing the motor stroke length to change the volume created within the diaphragm cavity, or by increasing the speed of the motor.

Cartridge 306 may include a diaphragm 358 in diaphragm chamber 356. Movement of diaphragm 358 away from valves 354 and 360 opens valve 354 and draws gas through valve 354 into diaphragm chamber 356, as shown by the arrow in FIG. 3. Valve 354 may be pulled open when diaphragm 358 moves away from valves 354 and 360, which may draw gas from the peritoneal cavity, through output tubing and into diaphragm chamber 356, as shown by the arrow in FIG. 3. Valve 360 may be pulled closed when diaphragm 358 moves away from valves 354 and 360, which may prevent gas from exiting or entering diaphragm chamber 356 through valve 360.

Movement of diaphragm 358 toward valves 354 and 360 opens valve 360 and pushes gas from diaphragm chamber 356, through valve 360 and out of cartridge 306 through connection 352, as shown by the arrows in FIG. 4. Movement of diaphragm 358 toward valves 354 and 360 closes valve 354, which may prevent pushing gas out of diaphragm chamber 356 through connection 350. Reciprocal movement of diaphragm 358 toward and away from valves 354 and 360 draws gas from the peritoneal cavity, through any filter or liquid trap in the output tubing, and pushes gas back into the peritoneal cavity through the input tubing.

FIGS. 5A-5D, 6A-6D, and 7A-7H show other example embodiments of cartridges for use in a gas recirculation pump, such as recirculation pump 205 described in relation to FIG. 2. The components and operational characteristics of the cartridges shown in FIGS. 5A-5D, 6A-6D, and 7A-7H may be similar to cartridge 306, described above.

FIG. 5A shows an exploded view of cartridge 506. Cartridge 506 includes connections 550, 552, valves 554, 560, diaphragm 558, and plunger 564. Valves 554, 560 may be umbrella valves. Connection 550 may be the gas inlet into cartridge 506. Connection 552 may be the gas outlet from cartridge 506. Plunger 564 may move diaphragm 558 toward valves 554, 560 in order to recirculate gas through the peritoneal cavity, as described above in reference to FIGS. 3 and 4.

FIG. 5B shows a non-exploded perspective view of cartridge 506. FIG. 5C shows a front view of cartridge 506. FIG. 5D shows a side view of cartridge 506.

FIG. 6A shows an exploded view of cartridge 606. Cartridge 606 includes connections 650, 652, valves 654, 660, diaphragm 658, and plunger 664. Valves 654, 660 may be umbrella valves. Connection 650 may be the gas inlet into cartridge 606. Connection 652 may be the gas outlet from cartridge 606. Plunger 664 may move diaphragm 658 toward valves 654, 660 in order to recirculate gas through the peritoneal cavity, as described above in reference to FIGS. 3 and 4.

FIG. 6B shows a non-exploded perspective view of cartridge 606. FIG. 6C shows a front view of cartridge 606 with exemplary dimensions. FIG. 6D shows a side view of cartridge 606 with exemplary dimensions. The dimensions and orientations of the components of cartridge 606 may vary depending on operational requirements.

FIGS. 7A-7H show multiple views of the gas inlet/outlet section of cartridge 706. FIG. 7A shows a perspective view of the gas inlet/outlet section of cartridge 706. FIG. 7B is a front view of the gas inlet/outlet section of cartridge 706. FIG. 7C is a bottom view of the gas inlet/outlet section of cartridge 706 with exemplary dimensions. FIG. 7D is a side view of the gas inlet/outlet section of cartridge 706. FIG. 7E is a back view of the gas inlet/outlet section of cartridge 706 with exemplary dimensions. FIG. 7F is a side cross-sectional view of the gas inlet/outlet section of cartridge 706 with exemplary dimensions. FIG. 7G is another side cross-section view of the gas inlet/outlet section of cartridge 706 with exemplary dimensions. FIG. 7H is bottom cross-section view of the gas inlet/outlet section of cartridge 706. The dimensions and orientations of the components of cartridge 706 may vary depending on operational requirements.

Figure 8:
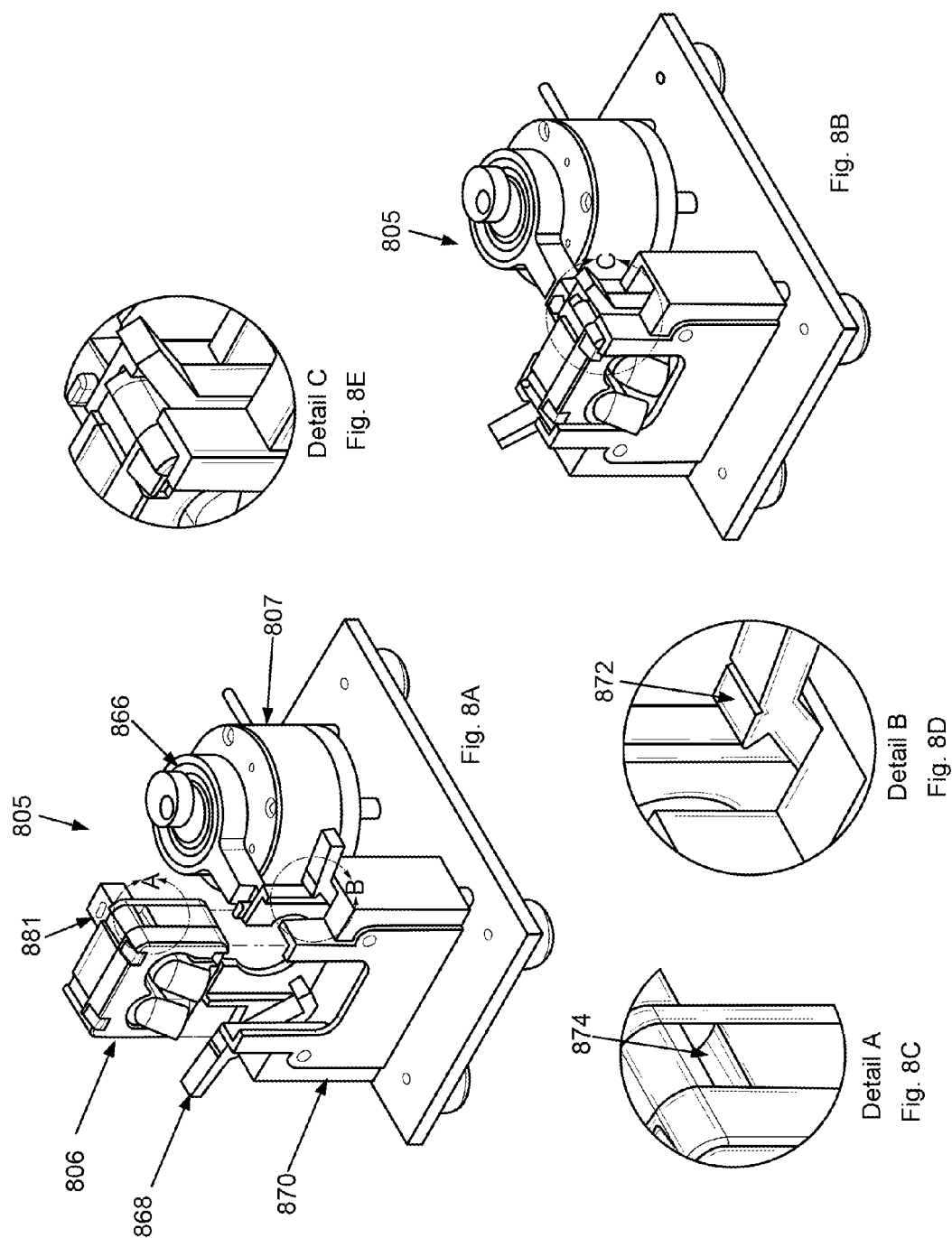
FIGS. 8A-8E are an example of an embodiment of a gas recirculation pump.

Referring to FIGS. 8A-8E, an embodiment of a recirculation pump 805 is shown. Recirculation pump 805 may include a cartridge 806, a motor 807, a crank assembly 866, locking arms 868, and a cartridge holder 870. The components and operational characteristics of recirculation pump 805 may be similar to recirculation pump 305, described above. Motor 807 may be connected to crank assembly 866 through a mechanical coupling. Motor 807 may provide rotational motion to crank assembly 866. Crank assembly 866 may convert the rotational motion to a reciprocal motion. The reciprocal motion of crank assembly 866 may move a diaphragm within cartridge 806, as described above with reference to FIG. 3. FIG. 8A shows cartridge 806 detached from recirculation pump 805. Cartridge 806 may be detached from recirculation pump 805 in order to sterilize or dispose of cartridge 806. Because cartridge 806 may be the only component of recirculation pump 805 that comes in contact with gas from a patient's peritoneal cavity, the remaining components of recirculation pump 805 may be reused with a different patient without risking patient safety. Cartridge 806 may be sterilized or disposed of after use with a patient and a new cartridge 806 may be inserted into recirculation pump 805 for the next patient.

FIG. 8B shows cartridge 806 inserted into cartridge holder 870 of recirculation pump 805. Cartridge 806 may be secured within recirculation pump 805 with locking arms 868. Locking arms 868 may include protrusions 872 designed to fit within recesses 874 located in cartridge 806. Protrusions 872 may be best seen in FIG. 8D. Recesses 874 may be best seen in FIG. 8C. Cartridge 806 may be secured within cartridge holder 870 when protrusions 872 are placed in recesses 874, as shown in FIG. 8F. Cartridge 806 may be released from cartridge holder 870 by depressing the ends of locking arms 868 and then lifting cartridge 806 from cartridge holder 870. The method of securing and releasing cartridge 806 from recirculation pump 805 may vary depending on operational requirements.

Figure 9:
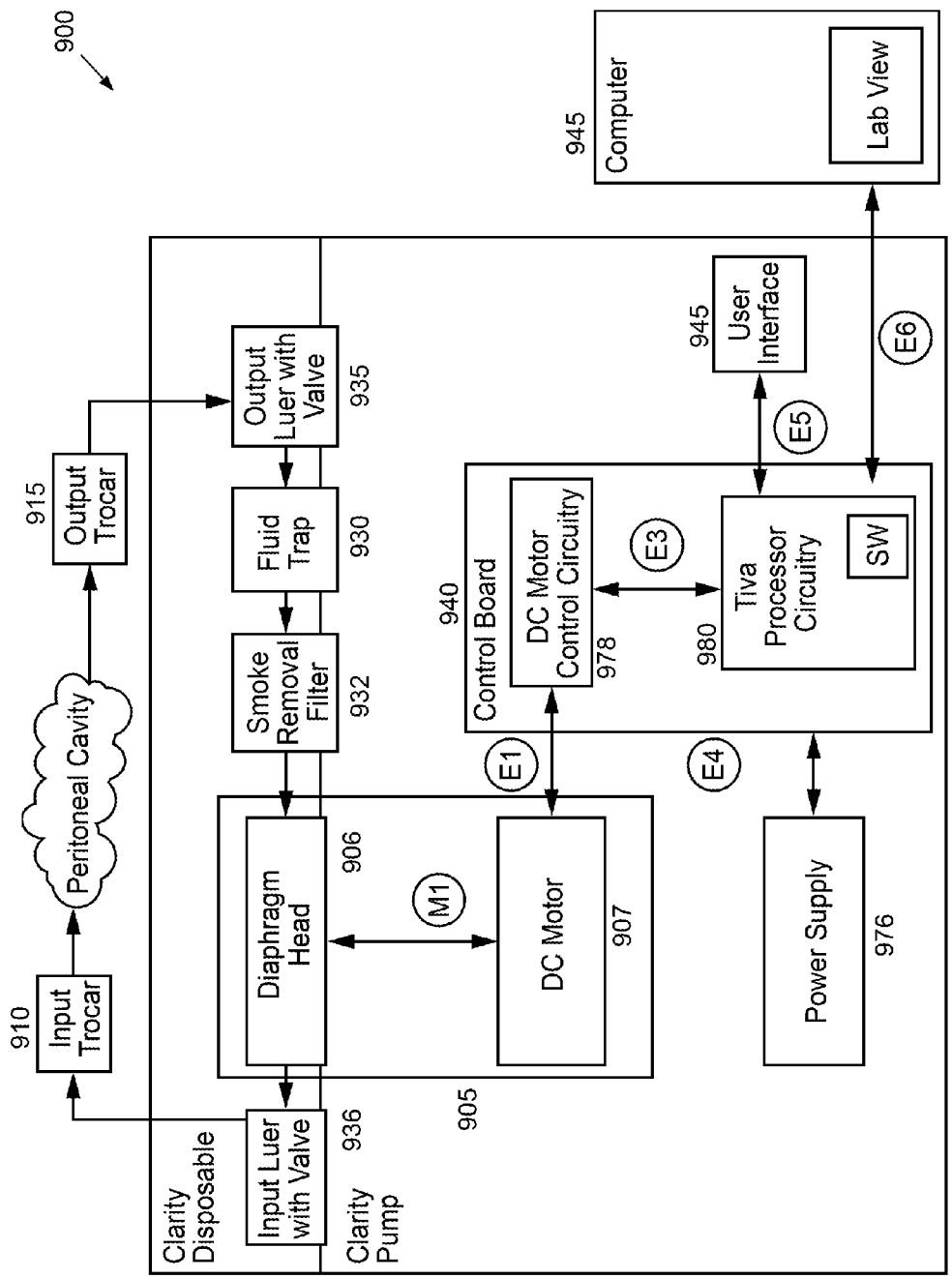
FIG. 9 is a block diagram of a gas recirculation system.

Referring to FIG. 9, an embodiment of a gas recirculation system 900 is shown. Gas recirculation system 900 may include similar components and operating characteristics as the gas recirculation systems described in FIGS. 1-8. Gas recirculation system 900 may include recirculation pump 905, pump cartridge 906, motor 907, input trocar 910, output trocar 915, valves 935 and 936, fluid trap 930, filter 932, controller 940, user interface 945, and power supply 976. Controller 940 may include DC motor control circuitry 978 and processor circuitry 980. User interface 945 may include a computer with software, such as LabView®, to control some or all components of gas recirculation system 900.

Gas recirculation system 900 may monitor the load placed on motor 907 in order to detect faults or safety issues with gas recirculation system 900. The load on motor 907 may be monitored by measuring the current change across a resistor located in the power path of motor 907, such as by connecting the resistor to an A-D converter to measure the current. The current will change as the load on motor 907 changes. The current measurement may be measured in real time or may include a delay. A change in current above or below a predetermined value may indicate that gas recirculation system 900 has a fault or safety issue and may initiate a shutdown of recirculation pump 905. Software may be included, for example in controller 940, to sense a change in current and to initiate a shutdown of motor 907.

The predetermined value of current that defines when a fault or safety issue occurs may be based on an average current when gas recirculation system 900 is operating normally. A current measurement above the average value may indicate a fault or safety condition, such as a disconnected valve 935 or 936 or an occlusion in the tubing connecting recirculation pump 905 to a patient's peritoneal cavity. For example, if the average current measured while motor 907 was driving a diaphragm in cartridge 906 during normal operation was 0.3 A, a measured current of 0.4 A may indicate an occlusion in the tubing connecting recirculation pump 905 to the patient's peritoneal cavity and a measured current of 0.5 A may indicate one of valves 935 or 936 were disconnected. Other methods or statistics could be used to define when a fault or safety condition occurs, such as by using a variance of measured currents or a comparison against a stored time template or frequency template. Additionally or alternatively, a processor in controller 940 may be capable of a Fast Fourier Transform to analyze the frequency content of the current measurement signal.

Interface M1 between pump cartridge 906 and motor 907 may be a mechanical interface. Interface M1 may be designed to operate adequately for continuous periods of time greater than the length of time gas recirculation system is used during a surgical procedure. For example, if the maximum length of time for a surgical procedure is four hours, interface M1 may be designed to operate continuously without error for eight hours.

The speed of motor 907 may be specified to allow the delivery of $CO_2$ gas at a rate of seven liters per minute. A motor suitable for motor 907 may include a Moog® brand high speed motor. The key operating parameters for motor 907 may be the torque, speed, and fault conditions. The operating current of motor 907 may be specified in several ways, such as the normal operating current, the fault current, the inflate state current, and the deflate state current. These current values may be used to define when motor 907 should be shutdown due to a fault or safety condition.

Interface E1 is between motor 907 and DC motor control circuitry 978. There may be eight lines in interface E1. The eight lines may include a line for each of the three drive phases of motor 907, a line each for three hall sensor pickups, a line to power the hall sensors, and a line for a ground. These eight lines may be common to multiple motor manufacturers.

Interface E3 is between DC motor control circuitry 978 and processor circuitry 980. There may be multiple lines in this interface depending on the method of speed control and feedback.

The speed of motor 907 may be controlled using two methods: voltage and digital control of the motor. The first method using voltage control would result in the processor circuitry 980 sending a voltage to the control circuitry 978 via a potentiometer or pulse width modulated signal. For reference, in this method the full speed of motor 907 may be reached by having the processor circuitry 980 provide the voltage of 3.25V to the motor control circuitry. The second method would involve in the processor circuitry 980 sending a digital signal to the motor control circuitry 978.

Gas recirculation system 900 may detect two fault states that are recoverable, such as the inflate fault state and the deflate fault state. Other fault states may occur that are not recoverable, such as a problem with motor 907. The inflate fault state may be when the gas circuit on the suction side of gas recirculation pump 905 is broken such that ambient air is drawn into gas recirculation system 900, for example if valve 935 is disconnected from output trocar 915. Such a state is named "inflate" because recirculation pump 905 may inflate the patient's peritoneal cavity with ambient air if recirculation pump 905 is not shutdown. An alternative to shutting down recirculation pump 905 if an inflate fault state occurs may be to reduce the gas flow through recirculation pump 905 to a small amount in order to minimize the amount of ambient air pumped into the peritoneal cavity. The deflate fault state may be when the gas circuit on the discharge side of gas recirculation pump 905 is broken such that gas from the peritoneal cavity is pumped into the ambient environment, for example if valve 936 is disconnected from input trocar 910. Such a state is named "deflate" because the peritoneal cavity may begin to deflate due to the loss of gas from gas recirculation system 900. A deflate fault state may cause the activation of an insufflator connected to the peritoneal cavity in order to maintain a desired inflation level or pressure in the peritoneal cavity.

Gas recirculation system 900 may be controlled through user interface 945. User interface 945 may be located in gas recirculation system 900 and/or in a computer connected to gas recirculation system 900. User interface may be multimode interface which may be controlled by software, such as LabView®. The first mode may be Output and the second mode may be Control. In Output mode, the processor in controller 940 may output information regarding monitoring motor 907. Such information may include motor speed (RPM), current (mA), voltage (V), and motor state.

Referring to FIGS. 10A-10B, an embodiment of a gas recirculation system 1000 is shown. Gas recirculation system 1000 may include similar components and operating characteristics as the gas recirculation systems described in FIGS. 1-9. Gas recirculation system 1000 may include a magnetic coupling between the diaphragm actuator 1081 and the motor coupling arm 1082 such that when the pump cartridge 1006 is inserted into position, a magnet on the diaphragm actuator 1081 is drawn to a magnet on the motor coupling arm 1082. Once the magnets are drawn together, the diaphragm actuator 1081 will follow the motor coupling arm 1082 up and down, causing pumping action in the pump cartridge 1006 (as discussed above), as the motor coupling arm 1082 moves up and down. The magnetic coupling may be an electromagnet that is cycled on and off to create and release the coupling between the diaphragm actuator 1081 and the motor coupling arm 1082, such as for removal of the pump cartridge 1006. Alternatively, the magnetic coupling may be a non-electromagnet. FIG. 10A shows the pump cartridge 1006 with a magnet on the diaphragm actuator 1081 before it is inserted and coupled to the motor coupling arm 1082. FIG. 10B shows the pump cartridge 1006 after it is inserted and the diaphragm actuator 1081 is magnetically coupled to the motor coupling arm 1082.

Alternatively, rather than using a motor with a crank arm to move the diaphragm actuator 1081 up and down, an oscillating magnetic field could be used to move a magnet attached to or embedded in the diaphragm actuator 1081 in order to move the diaphragm actuator 1081 up and down and create a pumping action in the pump cartridge 1006. Additionally or alternatively, a spring located within the pump cartridge 1006 could provide upward motion of the diaphragm, while a motor with a crank arm could provide the downward motion. Such an arrangement may eliminate the need to couple the diaphragm with the motor crank arm.

FIGS. 11A-11F disclose an embodiment of valves connecting the input and output tubing to trocars, such as valves 135, 235, 236, 935, and 936. Valve 1135 in FIG. 11A may include a rotatable collar with a movable section, such that when the valve 1135 is firmly connected the valve 1135 is open to allow gas flow and when disconnected prevents gas flow. FIG. 11A shows an exploded view of valve 1135, which may include a male luer lock fitting 1137 that joins with a female luer fitting (not shown) and rotates to allow gas flow. Valve 1135 may also include a sleeve and tubing connection 1138 to connect to input or output tubing, an o-ring to prevent leakage, and a part to hold the remaining components in place. FIG. 11B shows an end view of valve 1135 and FIG. 11C shows a side view of valve 1135. FIGS. 11D, 11E, and 11F show section views of valve 1135. FIG. 11F shows tabs 1139 that prevent over-rotation of the male luer lock 1137 fitting portion of valve 1135.

Figure 12:
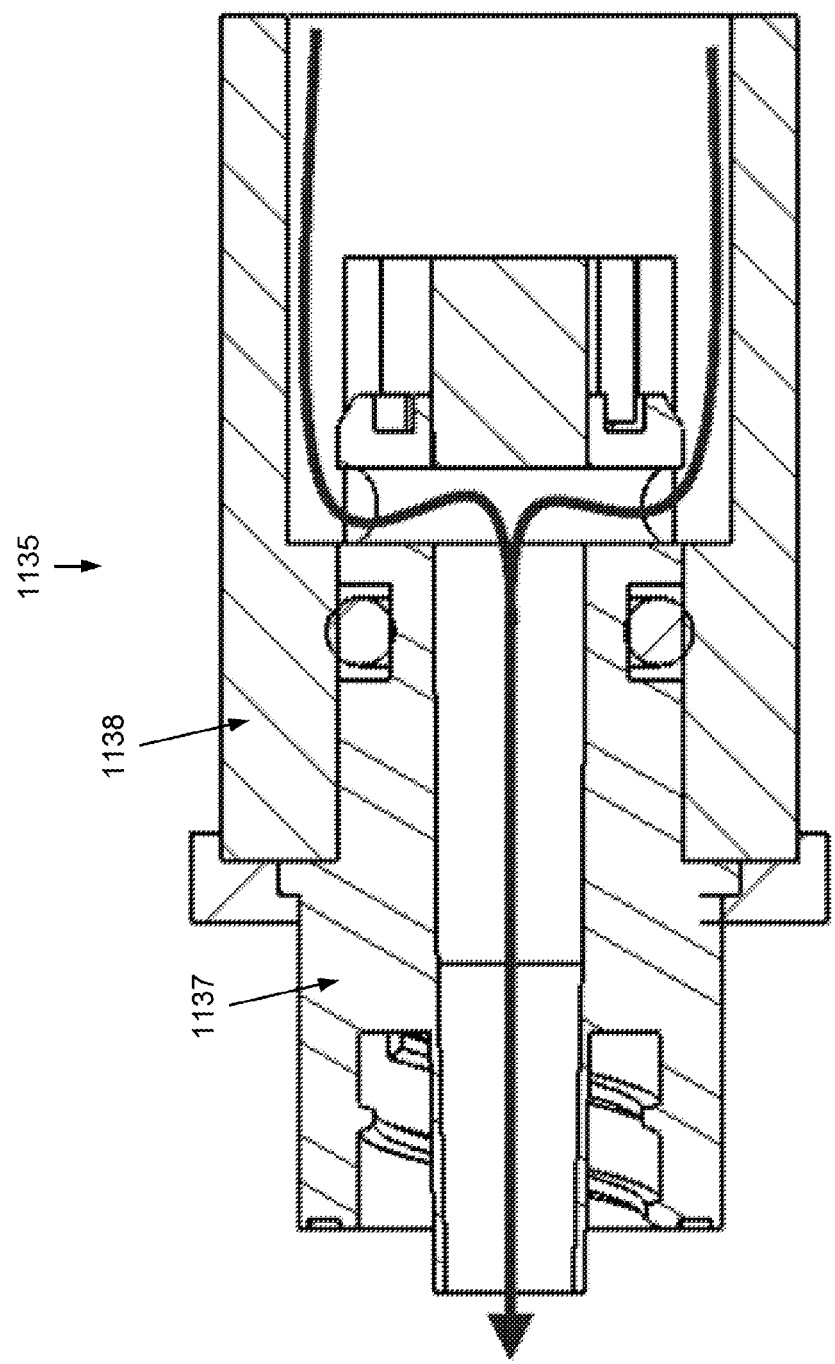
FIG. 12 is a cross-section of an embodiment of a connecting element used in a gas recirculation system.

FIG. 12 discloses a sectional view of valve 1135 in the open flow configuration. The arrows in FIG. 12 disclose the gas flow path through valve 1135 when male luer lock fitting 1137 is rotated to allow gas flow. When valve 1135 is connected to a trocar, the male luer lock fitting 1137 rotates inside a stationary sleeve 1138, aligning openings in the male luer lock fitting 1137 with openings in the sleeve 1138 and allowing gas to pass through. When the valve 1135 is disconnected, the openings become misaligned and block the flow of gas.

Figure 13:
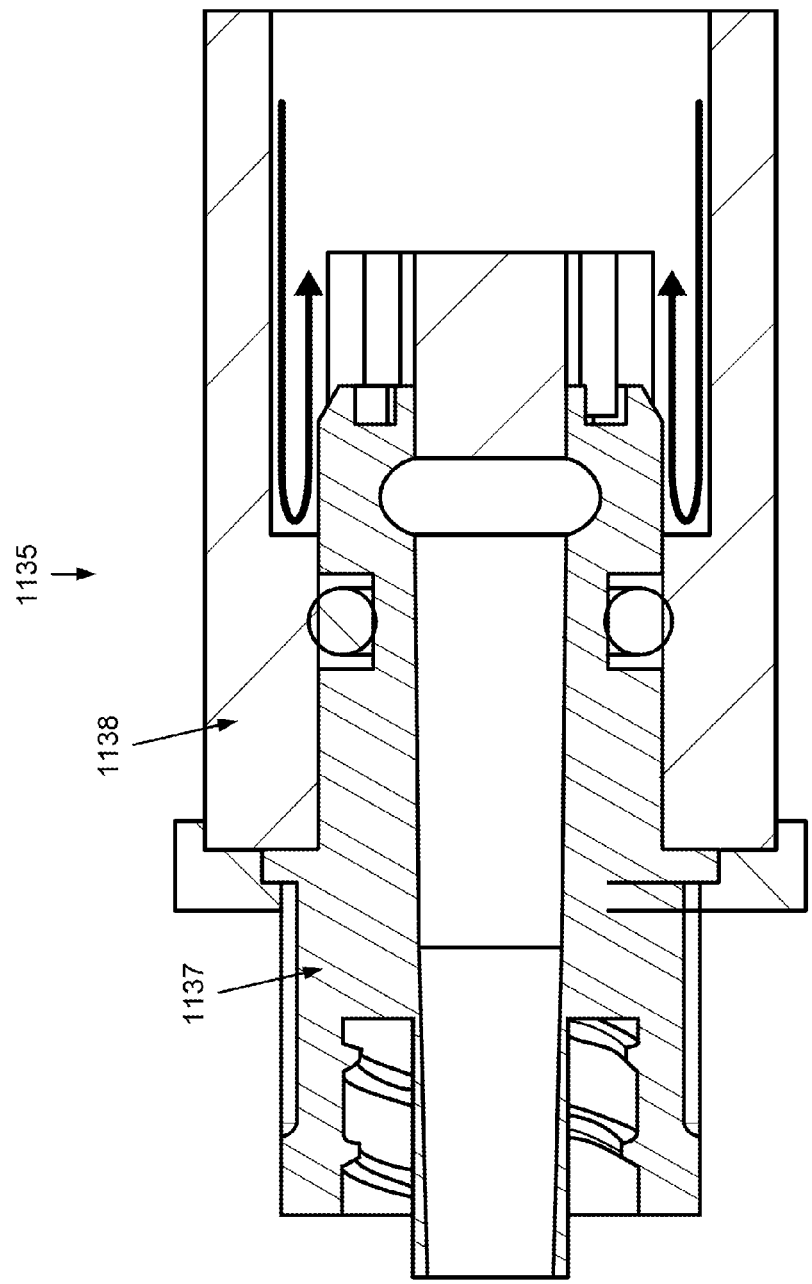
FIG. 13 is a cross-section of another embodiment of a connecting element used in a gas recirculation system.

FIG. 13 discloses a sectional view of valve 1135 in the closed flow configuration. The arrows in FIG. 13 disclose the gas flow path stopping in valve 1135 when male luer lock fitting 1137 is rotated to prevent fluid flow.

Figure 14:
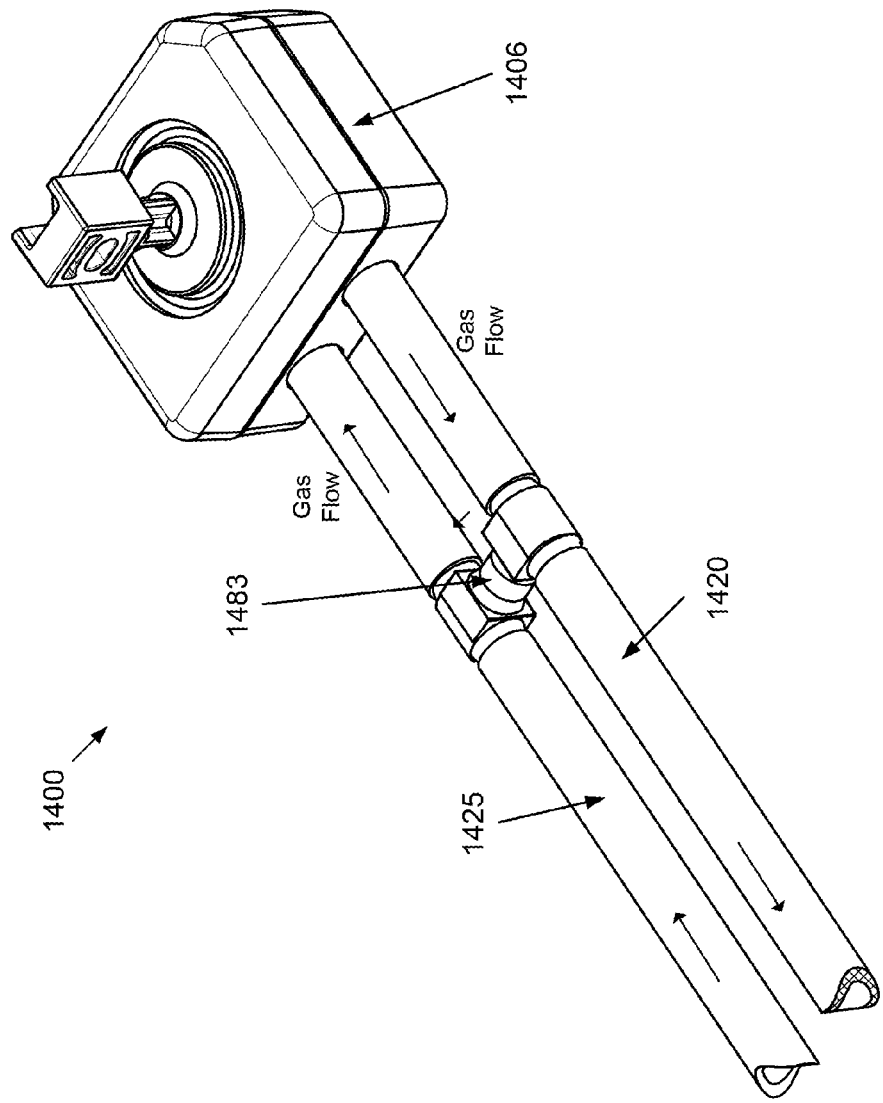
FIG. 14 is an example of an embodiment of a bypass valve used in a gas recirculation system.

FIG. 14 discloses an embodiment of a gas recirculation system 1400. Gas recirculation system 1400 may include similar components and operating characteristics as the gas recirculation systems described in FIGS. 1-13. Gas recirculation system 1400 may include a bypass valve 1483 that is located between output tubing 1425 and input tubing 1420. Arrows located in FIG. 14 may show the gas flow paths. Bypass valve may be normally closed such that there is no gas flow path between output tubing 1425 and input tubing 1420. When bypass valve 1483 is open it may create a gas flow path from input tubing 1420 to output tubing 1425 as shown by the arrows in FIG. 14. The gas flow path from input tubing 1420 to output tubing 1425 may create a circulating gas loop around the pump cartridge 1406 that may limit the downstream pressure that can be generated during the pumping cycle. For example, opening bypass valve 1483 may divert a portion of the gas flow from the pump cartridge 1406 into the output tubing 1425, which may prevent a pressure increase downstream of bypass valve 1483. Bypass valve 1483 may be a one-way pressure relieve valve, such as a Minivalve or a Halkey/Roberts® valve, such as a Duck Bill valve or a Spring Loaded valve. Bypass valve 1483 can be selected to open automatically based on the pressure present at the inlet side of bypass valve 1483, or at another location downstream of pump cartridge 1406. For example, bypass valve 1483 can be selected to open at a pressure as low as 0.1 psi to a pressure higher than 10 psi, depending on the application. It may be preferred that bypass valve 1483 open when the pressure is approximately in the range of 0.15 psi to 0.55 psi.

FIGS. 15A-B disclose an embodiment of a moisture trap, such as moisture traps 130, 230, and 930. Moisture trap 1530 in FIGS. 15A-B may be located in the output tubing (not shown) where gas flows from the patient to the recirculation pump (not shown), as shown by the arrows in FIG. 15B. FIG. 15B shows a section view of moisture trap 1530 that includes tube 1584 that extends within moisture trap 1530. Tube 1584 begins at the gas inlet side of moisture trap 1530 and may extend toward the outlet of moisture trap 1530, but may not contact the outlet of moisture trap 1530 such that there is a gap between the end of tube 1584 and the outlet of moisture trap 1530. The gap may allow liquid located within the gas to rain out before the gas reaches the outlet of moisture trap 1530. The liquid that is removed from the gas may collect within moisture trap 1530. The size of the gap between the end of tube 1584 and the outlet of moisture trap 1530 may be varied based on the application. For example, applications with higher gas velocities may require a larger gap to allow the liquid in the gas to rain out, whereas applications with relatively lower gas velocities may require a smaller gap to allow the liquid in the gas to rain out. Moisture trap 1530 may not include absorbent media to collect the liquid within moisture trap 1530. Moisture trap 1530, and its components, may be constructed of any suitable material to be in contact with liquid, such as plastic or metal.

FIGS. 16A-B disclose another embodiment of a moisture trap, such as moisture traps 130, 230, 930, and 1530. Moisture trap 1630 in FIGS. 16A-B may be located in the input tubing (not shown) where gas flows from the recirculation pump (not shown) to the patient, as shown by the arrows in FIG. 16B. FIG. 16B shows a section view of moisture trap 1630 that includes input tube 1685 and output tube 1685 that both extend within moisture trap 1630. Input tube 1684 begins at the gas inlet side of moisture trap 1630 and may extend toward the outlet of moisture trap 1630. Output tube 1685 begins at the gas outlet side of moisture trap 1630 and may extend toward the inlet of moisture trap 1630. Input tube 1684 and output tube 1685 may extend past each other within moisture trap 1630, creating an overlap as shown in FIG. 16B, such that gas entering moisture trap 1630 from inlet tube 1684 cannot flow directly into output tube 1685 without first flowing through the interior of moisture trap 1630. FIG. 16B shows that inlet tube 1684 and outlet tube 1685 may include bends such that portions of the tubes overlap while the inlet of inlet tube 1684 and the outlet of outlet tube 1685 remain axially aligned. Liquid within the gas may rain out while it is flowing through the interior of moisture trap 1630 and before it flows out of moisture trap 1630 through output tube 1685. The liquid that is removed from the gas may collect within moisture trap 1630. Moisture trap 1630 may not include absorbent media to collect the liquid within moisture trap 1630. Moisture trap 1630, and its components, may be constructed of any suitable material to be in contact with liquid, such as plastic or metal.

FIGS. 17A-C disclose an embodiment a gas recirculation system 1700. Gas recirculation system 1700 may include similar components and operating characteristics as the gas recirculation systems described in FIGS. 1-16. Gas recirculation system 1700 may include recirculation pump enclosure 1786 that houses some of the components of gas recirculation system 1700, such as a recirculation pump 1705, pump cartridge 1706, motor 1707, controller 1740, user interface 1745, power supply 1776, DC motor control circuitry 1778, and processor circuitry 1780.

FIG. 17A discloses gas recirculation system 1700 with the cartridge door open showing pump cartridge 1706 installed inside enclosure 1786. FIG. 17C is a detailed section view of gas recirculation system 1700 showing the pump cartridge locking mechanism 1787. Pump cartridge locking mechanism 1787 may include spring 1788 with ball 1789 located at one end of spring 1788. Spring 1788 may exert force on pump cartridge 1706 through ball 1789, which may lock pump cartridge 1706 within enclosure 1786. Alternatively, spring 1788 may exert force directly on pump cartridge 1706 without ball 1789.

Figure 18B:
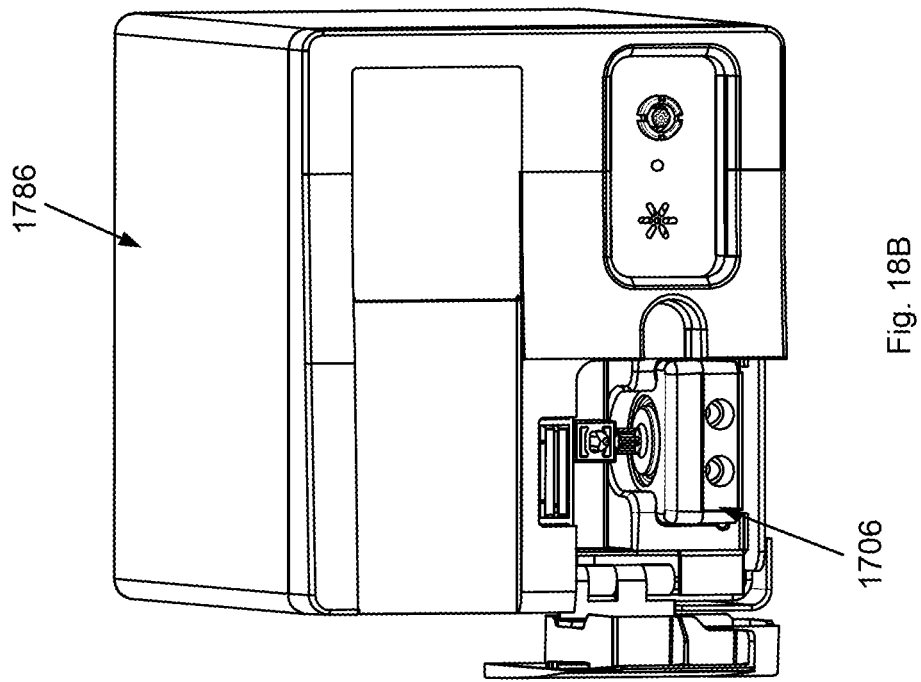
FIGS. 18A and 18B are an example of another embodiment of an enclosure for a gas recirculation system.
Figure 18A:
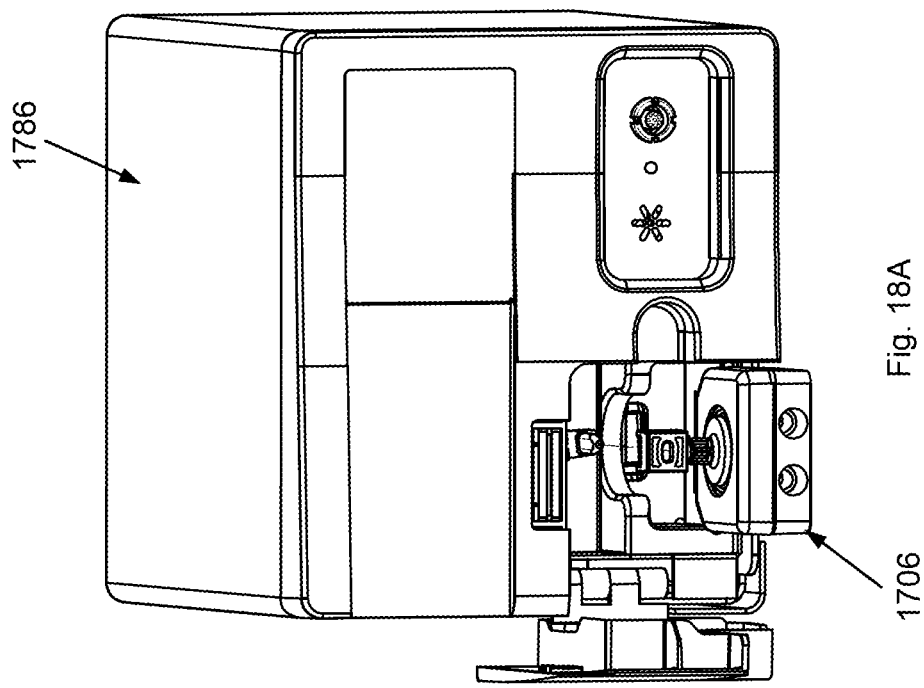

FIG. 18A is a perspective view of gas recirculation system 1700 with pump cartridge 1706 in a pre-insertion position. FIG. 18B is a perspective view of gas recirculation system 1700 with pump cartridge 1706 installed in enclosure 1786.

Figure 19B:
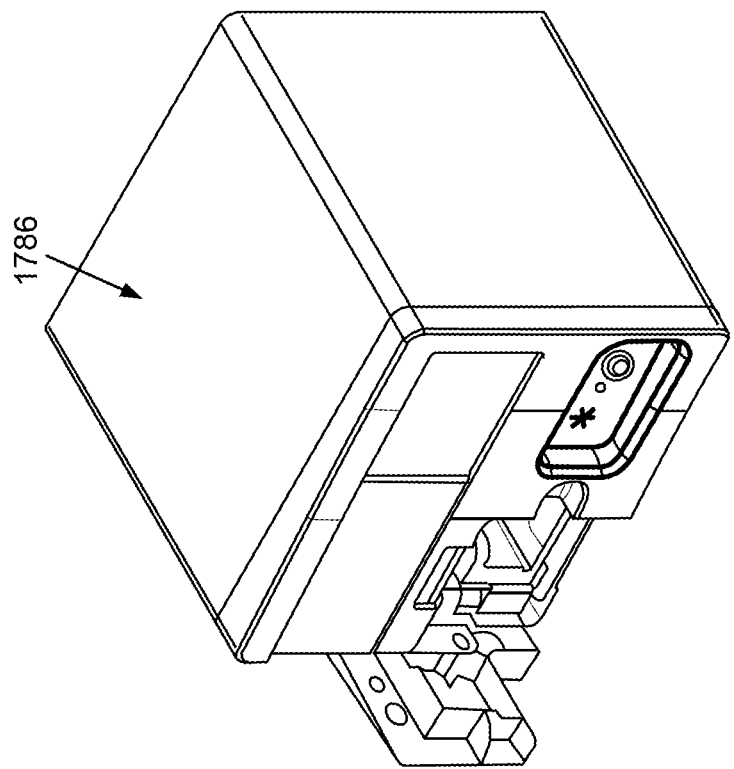
FIGS. 19A and 19B are an example of another embodiment of an enclosure for a gas recirculation system.
Figure 19A:
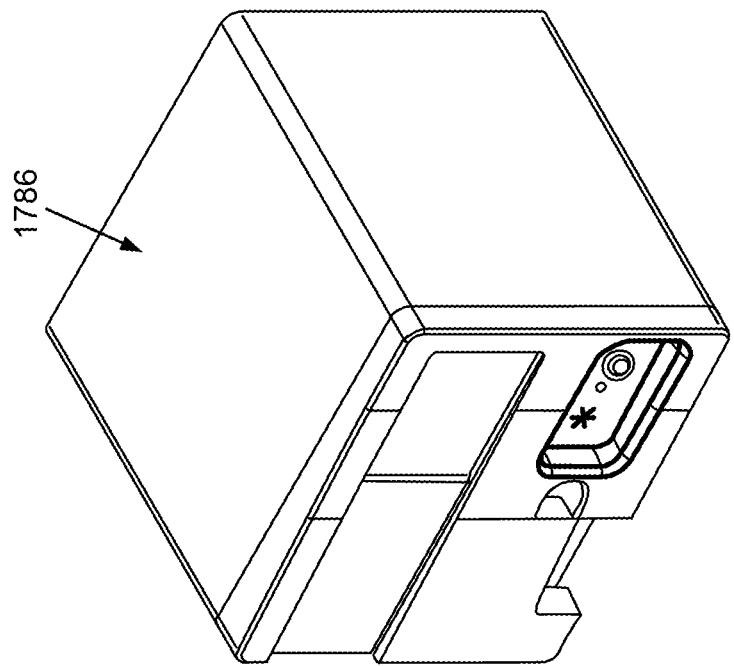
Figure 21D:
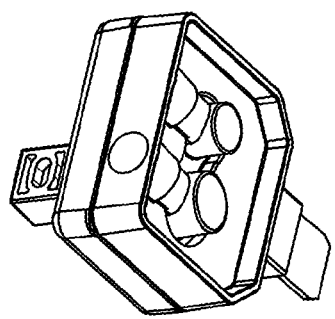
FIGS. 21A-21H are another example of an embodiment of a gas recirculation pump cartridge.
Figure 21H:
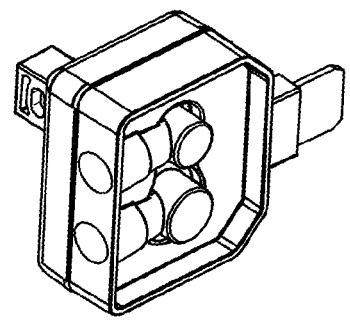
Figure 21C:
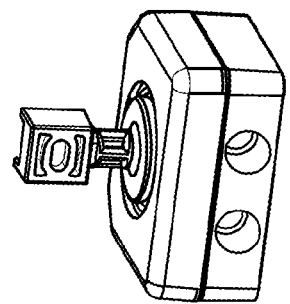
Figure 21G:
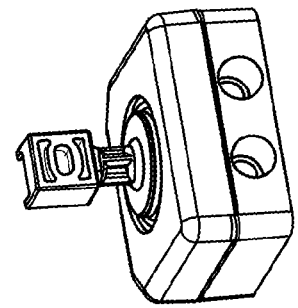
Figure 21B:
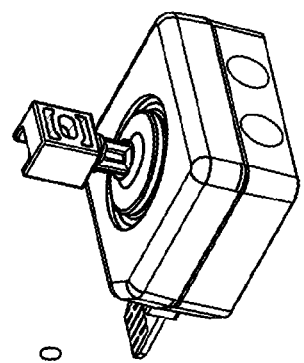
Figure 21F:
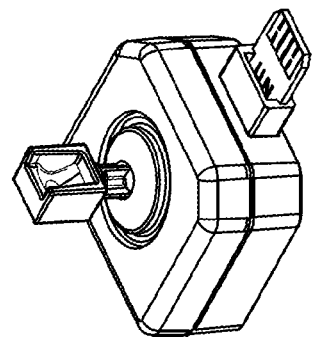
Figure 21A:
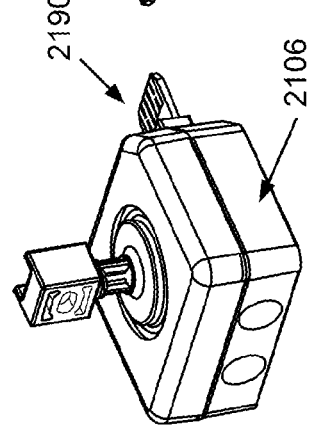
Figure 21E:
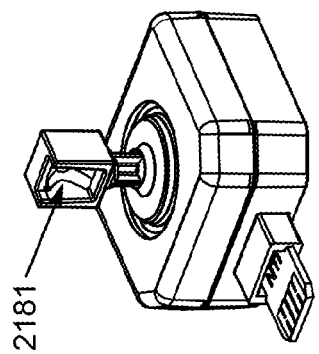

FIG. 19A is a perspective view of gas recirculation system 1700 with the cartridge door closed. FIG. 19B is a perspective view of gas recirculation system 1700 with the cartridge door open and without pump cartridge 1706.

FIGS. 20A-20F disclose views of gas recirculation system 1700 with the cartridge door closed. The dimensions shown in FIGS. 20 A-20F are exemplary and may be modified based on the application of gas recirculation system 1700.

FIGS. 21A-21H disclose an embodiment a gas recirculation system 2100. Gas recirculation system 2100 may include similar components and operating characteristics as the gas recirculation systems described in FIGS. 1-20. Gas recirculation system 2100 may include pump cartridge 2106 with a coded connector 2190. Connector 2190 may be described in U.S. Pat. No. 9,283,334, which is hereby incorporated by reference. Connector 2190 may be able to identify if the correct pump cartridge 2106 is connected to recirculation pump 2105, if pump cartridge 2106 has been used previously, or to select and set gas recirculation system 2100 to operate according to special settings, such as flow rates. FIGS. 21A-21H show perspective views of pump cartridge 2106 with connector 2190.

FIGS. 22A-B disclose an embodiment a gas recirculation system 2200. Gas recirculation system 2200 may include similar components and operating characteristics as the gas recirculation systems described in FIGS. 1-21. Gas recirculation system 2200 may include components that allow the pump cartridge 2206 (not shown) to be coupled with the motor coupling arm 2282 in a "blind" manner, such that a user may insert the pump cartridge 2206 into the gas recirculation system enclosure 2286 (not shown) without knowing the exact location of the motor coupling arm 2282 and without bending over to look inside enclosure 2286 to see the location of the motor coupling arm 2282. FIG. 22A shows a coupling shaft 2291 extending from the front of the motor coupling arm 2282. Coupling shaft 2291 may include a tapered end portion to aid insertion of the coupling shaft 2291 into the corresponding opening in diaphragm actuator 2281 (not shown in FIGS. 22A-B, shown in FIGS. 5, 6, 8, and 21). Diaphragm actuator 2281 may include a corresponding tapered opening (as shown in FIG. 21). A locating pin 2292 may extend from the back of the motor coupling arm 2282. Locating pin 2292 may fit within locating slot 2293. FIG. 22B shows a detail view of the coupling shaft 2291 and locating pin 2292 extending from the motor coupling arm 2282. Locating slot 2293 may be found in the mount for motor 2207 or other stationary portion of enclosure 2286. Locating pin 2292 will move up and down in locating slot 2293 as motor 2207 causes motor coupling arm 2282 to move up and down. Locating slot 2293 will restrict the side to side motion of locating pin 2292. Because locating pin 2292 is connected with motor coupling arm 2282, the restricted side to side motion of locating pin 2292 will ensure that motor coupling arm 2282 and coupling shaft 2291 remain in approximately the same vertical plane regardless of where motor coupling arm 2282 is located when motor 2207 stops. Accordingly, a user may easily insert pump cartridge 2206 into enclosure 2286 and couple diaphragm actuator 2281 with motor coupling arm 2282.

FIGS. 23A-F disclose views of portions of gas recirculation system 2200. FIG. 23A shows a front view of the mount for motor 2207 and motor coupling arm 2282 with coupling shaft 2291. FIG. 23B shows a section side view of the mount for motor 2207 along with motor 2207, coupling shaft 2291, and locating pin 2292. FIG. 23C shows a detail view of coupling shaft 2291 and locating pin 2292 found on the front and back, respectively, of motor coupling arm 2282. FIG. 23D shows a side view of the mount for motor 2207 along with motor 2207 and locating pin 2292 as it extends through locating slot 2293. FIG. 23E shows a back view of the mount for motor 2207 along with motor 2207 and locating pin 2292 as it extends through locating slot 2293. FIG. 23F shows a detail back view of locating pin 2292 as it extends through locating slot 2293.

FIGS. 24A-B disclose an embodiment a gas recirculation system 2400. Gas recirculation system 2400 may include similar components and operating characteristics as the gas recirculation systems described in FIGS. 1-23. Gas recirculation system 2400 may include components to evacuate $CO_2$ gas from a patient's peritoneal cavity after laparoscopic surgery is completed. Typically, when laparoscopic surgery is completed, a luer connection on a trocar that inserted into the patient is opened, which allows $CO_2$ gas from within a patient's peritoneal cavity to escape into the operating room. Undesirably, the escaping $CO_2$ gas is not filtered and may contain aerosolized chemicals, particles, bacteria, etc. that remains from the operative procedure.

Gas recirculation system 2400 may include three-way valve 2494 located in input tubing 2420. Input tubing 2420 flows to the patient. FIG. 24A shows that three-way valve 2494 may be located downstream of filter 2432 so that any gas flowing through three-way valve 2494 has already had impurities filtered out. FIG. 24B is a detail view of gas recirculation system 2400 showing three-way valve 2494, input tubing 2420, output tubing 2425, and filter 2432. At the end of a surgical procedure, before the recirculation tubing 2420, 2425 is removed and while the recirculation pump 2405 is still operating, three-way valve 2494 may be configured to prevent gas flow to the patient and to allow gas flow to the operating room. In this manner, the recirculation pump 2405 will pump out the $CO_2$ gas from within the patient's peritoneal cavity with filter 2432 preventing any contamination from leaving the patient. Utilizing three-way valve 2494 to allow gas flow to the operating room, rather than simply disconnecting input tubing 2420 from the patient, ensures that the only gas from the patient entering the operating room is filtered through filter 2432 first by maintaining all the gas connections with the patient that existed during the surgical procedure. Utilizing three-way valve 2494 to remove the $CO_2$ gas from the patient may reduce the risk to operating room staff without requiring an additional means for insuring the cleanliness of the escaping $CO_2$ gas.

Figure 25B:
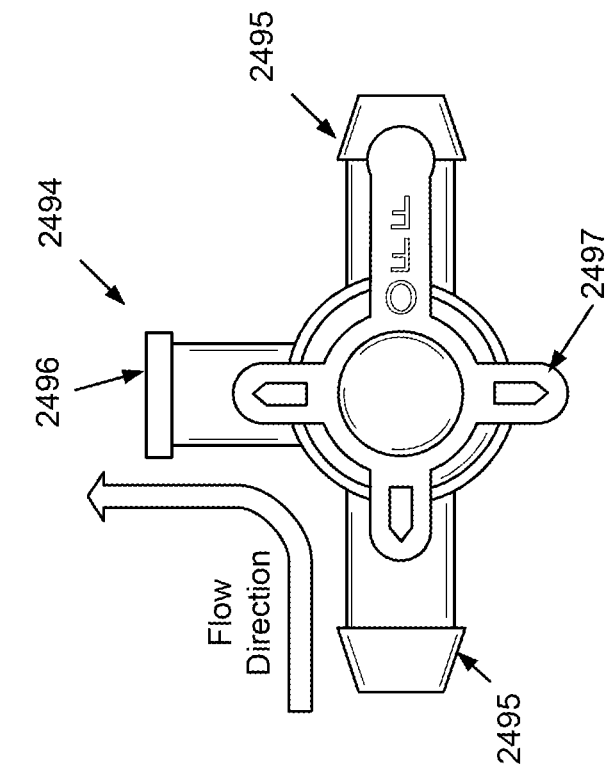
FIGS. 25A and 25B are an example of another embodiment of a three-way valve used in a gas recirculation system.
Figure 25A:
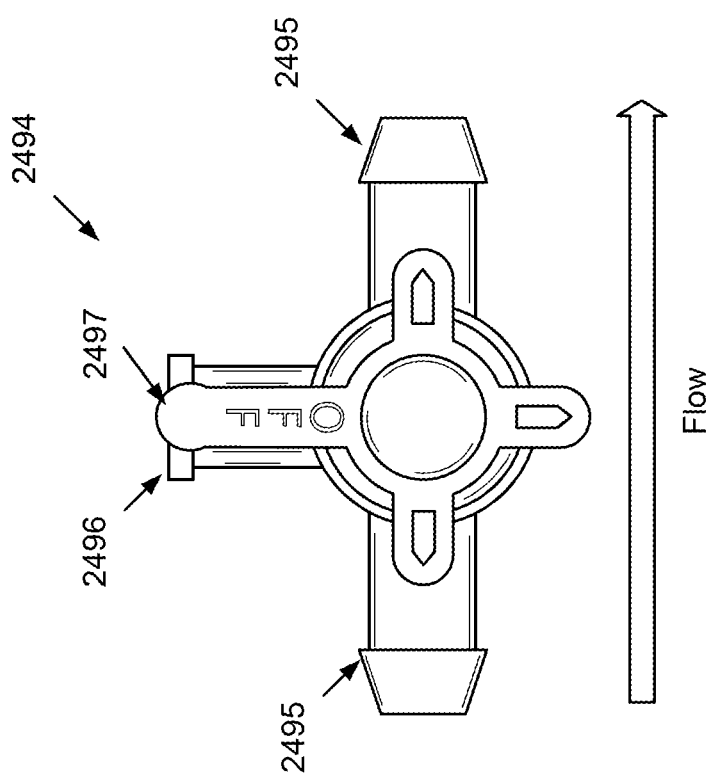

FIGS. 25A-B show three-way valve 2494 isolated from input tubing 2420. Three-way valve 2494 may include two in-line barbed fittings 2495 to connect with input tubing 2420. Three-way valve 2494 may also include a female luer connection 2496 oriented perpendicularly to the two in-line barbed fittings 2495. The female luer connection 2496 may be used for pressure relief purposes, such as to release $CO_2$ gas into the operating room. Three-way valve 2494 may also include a stopcock 2497 that rotates to adjust the open flow path of three-way valve 2494. As shown in FIG. 25, the closed flow path through three-way valve 2494 is indicated by the "OFF" portion of stopcock 2497. FIG. 25A shows three-way valve 2494 configured to allow gas flow through the two in-line barbed fittings 2495, which may be connected with input tubing 2420 leading to the patient. FIG. 25A may be the configuration used during recirculation function. The configuration of three-way valve 2494 in FIG. 25A may prevent gas from being released into the operating room. FIG. 25B shows three-way valve 2494 configured to allow gas flow out through the female luer connection 2496 and into the operating room. FIG. 25B may be the configuration used at the end of the surgical procedure when gas is being evacuated from the patient. The configuration of three-way valve 2494 in FIG. 25B may prevent gas flowing to the patient.

While various embodiments of the invention have been described, it will be apparent to those of ordinary skill in the art that many more embodiments and implementations are possible within the scope of the invention. The elements of the various embodiments disclosed may be combined and adapted to create a system with some or all of the operating characteristics and advantages of the embodiments. Any such combinations are herein disclosed in this application.

The invention claimed is:

1. A gas recirculation system for use in an endoscopic surgical procedure, the system comprising:
   a pump comprising:
      a motor; and
      a pump cartridge coupled to the motor, wherein the pump cartridge includes a gas input connection and a gas output connection, wherein the pump cartridge is detachable from the motor, and wherein the pump cartridge is sealed such that a gas within the pump cartridge cannot contact the motor, wherein the pump cartridge includes a first chamber in fluid communication with the gas input connection and a second chamber in fluid communication with the gas output connection, wherein a diaphragm is disposed between the first chamber and the second chamber;
   a first tube in fluid communication with the gas input connection, wherein the first tube is configured to be connectable to surgical equipment that is insertable into a peritoneal cavity; and
   a second tube in fluid communication with the gas output connection, wherein the second tube is configured to be connectable to surgical equipment that is insertable into a peritoneal cavity;
   wherein the pump is configured to draw gas into the gas input connection from a peritoneal cavity through the first tube and to discharge gas out of the gas output connection and into a peritoneal cavity through the second tube.

2. The gas recirculation system of claim 1, further comprising a first valve in fluid communication with the gas input connection and a second valve in fluid communication with the gas output connection, wherein the first valve prevents gas exiting the pump cartridge via the gas input connection and wherein the second valve prevents gas entering the pump cartridge via the gas output connection.

3. The gas recirculation system of claim 1, wherein the diaphragm is operable to shift from a first position to a second position in order to draw a gas into the pump cartridge through the gas input connection and discharge gas out of the pump cartridge through the gas output connection.

4. The gas recirculation system of claim 1, wherein the pump cartridge is disposable.

5. The gas recirculation system of claim 1, further comprising a third valve in fluid communication with the gas input connection through the first tube and a fourth valve in fluid communication with the gas output connection through the second tube, wherein the third and fourth valves automatically close when disconnected.

6. The gas recirculation system of claim 1, further comprising a filter in fluid communication with the gas input connection or the gas output connection.

7. The gas recirculation system of claim 1, further comprising a fluid trap in fluid communication with the gas input connection or the gas output connection.

8. The gas recirculation system of claim 7, wherein the fluid trap is operable to absorb liquid droplets from a gas traversing the fluid trap and release moisture to the gas traversing the fluid trap.

9. The gas recirculation system of claim 8, wherein the gas traversing the fluid trap maintains a relative humidity in the range of 50% to 70%.

10. The gas recirculation system of claim 1, wherein the system is operable to achieve gas flow rates in the range of 4 and 10 liters per minute.

11. The gas recirculation system of claim 1, configured to communicate with an insufflator.

12. The gas recirculation system of claim 11, wherein the gas recirculation system is configured to be controlled by the insufflator.

13. The gas recirculation system of claim 1, wherein the gas recirculation system is located within an insufflator and utilizes a power supply, a processor, and a user interface of the insufflator.

14. The gas recirculation system of claim 1, wherein the motor has a rotatable motor shaft, the gas recirculation system further comprising:
a coupling arm rotatably coupled to the motor shaft;
a coupling shaft extending from the coupling arm;
a locating pin extending from the coupling arm, wherein the locating pin is configured to move within a slot as the motor shaft rotates such that the coupling shaft remains within a plane as the motor shaft rotates.

15. A gas recirculation system for use in an endoscopic surgical procedure, the system comprising:
a pump comprising:
a motor; and
a pump cartridge coupled to the motor, wherein the pump cartridge includes a gas input connection and a gas output connection, wherein the pump cartridge is detachable from the motor, and wherein the pump cartridge is sealed such that a gas within the pump cartridge cannot contact the motor;
a first tube in fluid communication with the gas input connection, wherein the first tube is configured to be connectable to surgical equipment that is insertable into a peritoneal cavity; and
a second tube in fluid communication with the gas output connection, wherein the second tube is configured to be connectable to surgical equipment that is insertable into a peritoneal cavity;
wherein the pump is configured to draw gas into the gas input connection from a peritoneal cavity through the first tube and to discharge gas out of the gas output connection and into a peritoneal cavity through the second tube;
a controller, wherein the controller is operable to detect a fault condition based on an amount of power delivered to the motor.

16. The gas recirculation system of claim 15, wherein the fault condition is selected from the group consisting of:
a disconnection in a gas circuit within the gas recirculation system;
a blockage in a gas circuit within the gas recirculation system;
a motor fault.

17. The gas recirculation system of claim 15, further comprising a user interface connected to the controller.

18. A medical system for use in an endoscopic surgical procedure, the system comprising:
an insufflator configured to provide gas to a peritoneal cavity;
an insufflation tube in fluid communication with the insufflator, wherein the insufflation tube is configured to be connectable to surgical equipment that is insertable into a peritoneal cavity;
a gas recirculation system comprising:
a pump comprising:
a motor; and
a pump cartridge coupled to the motor, wherein the pump cartridge includes a gas input connection and a gas output connection, wherein the pump cartridge is detachable from the motor, and wherein the pump cartridge is sealed such that a gas within the pump cartridge cannot contact the motor, wherein the pump cartridge includes a first chamber in fluid communication with the gas input connection and a second chamber in fluid communication with the gas output connection, wherein a diaphragm is disposed between the first chamber and the second chamber;
a first tube in fluid communication with the gas input connection, wherein the first tube is configured to be connectable to surgical equipment that is insertable into a peritoneal cavity; and
a second tube in fluid communication with the gas output connection, wherein the second tube is configured to be connectable to surgical equipment that is insertable into a peritoneal cavity;
wherein the pump is configured to draw gas into the gas input connection from a peritoneal cavity through the first tube and to discharge gas out of the gas output connection and into a peritoneal cavity through the second tube;
wherein the insufflator and the gas recirculation system are configured to recirculate gas from the peritoneal cavity and to maintain a pressure within the peritoneal cavity.

* * * * *